US007759059B2

(12) United States Patent
Choo et al.

(10) Patent No.: US 7,759,059 B2
(45) Date of Patent: Jul. 20, 2010

(54) NUCLEIC ACID BINDING PROTEINS

(75) Inventors: Yen Choo, London (GB); Aaron Klug, Cambridge (GB); Mark Isalan, London (GB)

(73) Assignee: Gendaq Limited, c/o Brobeck Hale and Dorr, London (GB)

( * ) Notice: Subject to any disclaimer, the term of this patent is extended or adjusted under 35 U.S.C. 154(b) by 710 days.

(21) Appl. No.: 11/515,369

(22) Filed: Aug. 31, 2006

(65) Prior Publication Data

US 2007/0161014 A1 Jul. 12, 2007

Related U.S. Application Data

(63) Continuation of application No. 10/853,437, filed on May 24, 2004, now Pat. No. 7,241,574, which is a continuation of application No. 09/424,488, filed as application No. PCT/GB98/01516 on May 26, 1998, now Pat. No. 6,866,997.

(51) Int. Cl.
*C12Q 1/68* (2006.01)
(52) U.S. Cl. .................... 435/6; 435/7.1; 435/91.1; 536/23.1
(58) Field of Classification Search .................... None
See application file for complete search history.

(56) References Cited

U.S. PATENT DOCUMENTS

| 4,990,607 | A | 2/1991 | Katagiri et al. |
| 5,096,814 | A | 3/1992 | Aivasidis et al. |
| 5,096,815 | A | 3/1992 | Ladner et al. |
| 5,198,346 | A | 3/1993 | Ladner et al. |
| 5,223,409 | A | 6/1993 | Ladner et al. |
| 5,243,041 | A | 9/1993 | Fernandez-Pol |
| 5,302,519 | A | 4/1994 | Blackwood et al. |
| 5,324,638 | A | 6/1994 | Tao et al. |
| 5,324,818 | A | 6/1994 | Nabel et al. |
| 5,324,819 | A | 6/1994 | Oppermann et al. |
| 5,340,739 | A | 8/1994 | Stevens et al. |
| 5,348,864 | A | 9/1994 | Barbacid |
| 5,350,840 | A | 9/1994 | Call et al. |
| 5,356,802 | A | 10/1994 | Chandrasegaran |
| 5,376,530 | A | 12/1994 | De The et al. |
| 5,403,484 | A | 4/1995 | Ladner et al. |
| 5,436,150 | A | 7/1995 | Chandrasegaran |
| 5,487,994 | A | 1/1996 | Chandrasegaran |
| 5,498,530 | A | 3/1996 | Schatz et al. |
| 5,578,483 | A | 11/1996 | Evans et al. |
| 5,597,693 | A | 1/1997 | Evans et al. |
| 5,639,592 | A | 6/1997 | Evans et al. |
| 5,674,738 | A | 10/1997 | Abramson et al. |
| 5,702,914 | A | 12/1997 | Evans et al. |
| 5,789,538 | A | 8/1998 | Rebar et al. |
| 5,792,640 | A | 8/1998 | Chandrasegaran |
| 5,869,618 | A | 2/1999 | Lippman et al. |
| 5,871,907 | A | 2/1999 | Winter et al. |
| 5,916,794 | A | 6/1999 | Chandrasegaran |
| 5,939,538 | A | 8/1999 | Leavitt et al. |
| 5,972,615 | A | 10/1999 | An et al. |
| 6,001,885 | A | 12/1999 | Vega et al. |
| 6,007,988 | A | 12/1999 | Choo et al. |
| 6,013,453 | A | 1/2000 | Choo et al. |
| 6,746,838 | B1 | 6/2004 | Choo et al. |
| 6,866,997 | B1 * | 3/2005 | Choo et al. .................... 435/6 |
| 7,241,573 | B2 | 7/2007 | Choo et al. |
| 7,241,574 | B2 | 7/2007 | Choo et al. |
| 2007/0077227 | A1 | 4/2007 | Choo et al. |

FOREIGN PATENT DOCUMENTS

| EP | 875 567 A2 | 11/1998 |
| WO | WO 95/19431 A1 | 7/1995 |
| WO | WO 96/06110 A1 | 2/1996 |
| WO | WO96/06166 * | 2/1996 |
| WO | WO 96/06166 A1 | 2/1996 |
| WO | WO 96/11267 A1 | 4/1996 |
| WO | WO 96/20951 A1 | 7/1996 |
| WO | WO 96/32475 A2 | 10/1996 |
| WO | WO 97/27212 A1 | 7/1997 |
| WO | WO 97/27213 A1 | 7/1997 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 99/36553 A2 | 7/1999 |
| WO | WO 99/41371 A1 | 8/1999 |
| WO | WO 99/42474 A2 | 8/1999 |
| WO | WO 99/45132 A1 | 9/1999 |
| WO | WO 99/47656 A2 | 9/1999 |
| WO | WO 99/48909 A2 | 9/1999 |

OTHER PUBLICATIONS

Agarwal et al., "Stimulation of Transcript Elongation Requires both the Zinc Finger and RNA Polymerase II Binding Domains of Human TFIIS," *Biochemistry*, 30(31):7842-7851 (1991).
Anato et al., "A thermodynamic study of unusually stable RNA and DNA hairpins," *Nuc. Acids. Res.*, 19(21):5901-5905 (1991).
Barbas, C. F., "Recent advances in phage display," *Curr. Opin. Biotech.*, 4:526-530 (1993).
Barbas et al., "Assembly of combinatorial antibody libraries on phage surfaces: The gene III site," *PNAS*, 88:7978-7982 (1991).
Barbas et al., "Semisynthetic combinatorial antibody libraries: A chemical solution to the diversity problem," *PNAS*, 89:4457-4461 (1992).
Bellefroid et al., "Clustered organization of homologous KRAB zinc-finger genes with enhanced expression in human T lymphoid cells," *EMBO J.*, 12(4):1363-1374 (1993).
Berg, J. M., "DNA Binding Specificity of Steriod Receptors," *Cell*, 57:1065-1068 (1989).
Berg, J. M., "Sp1 and the subfamily of zinc finger proteins with guanine-rich binding sites," *PNAS*, 89:11109-11110 (1992).
Berg et al., "The Galvanization of Biology: A Growing Appreciation for the Roles of Zinc," *Science*, 271:1081-1085 (1996).

(Continued)

*Primary Examiner*—Hope A Robinson
(74) *Attorney, Agent, or Firm*—Townsend and Townsend and Crew, LLP

(57) ABSTRACT

The application provides methods of designing zinc finger binding polypeptides for binding to particular target sequences comprising overlapping nucleotide quadruplets.

21 Claims, 8 Drawing Sheets

OTHER PUBLICATIONS

Figure 1B:
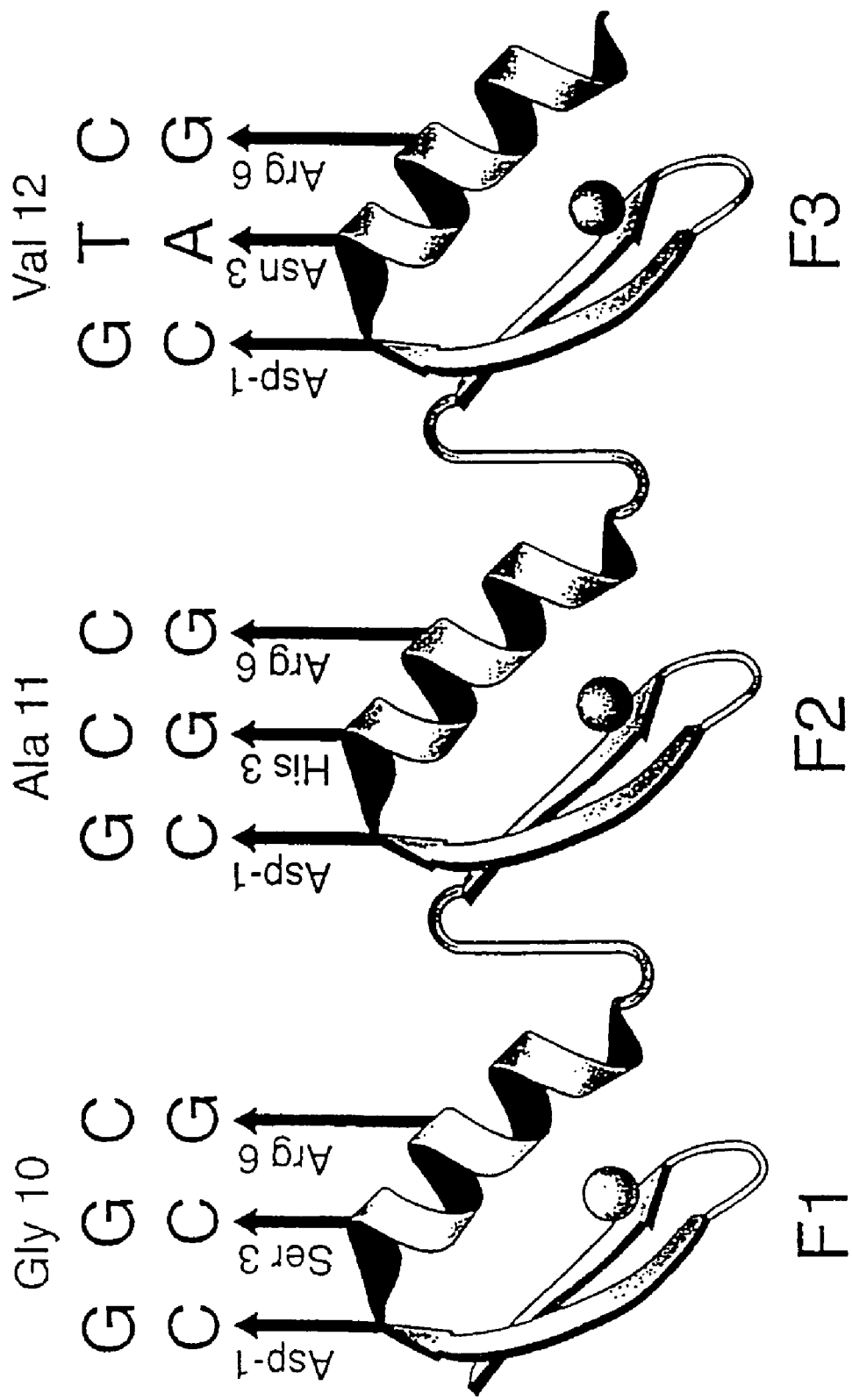

Berg, J. M., "Letting your fingers do the walking," *Nature Biotechnology*, 15:323 (1997).

Bergqvist et al., "Loss of DNA-binding and new transcriptional transactivation function in polyomavirus large T-antigen with mutation of zinc finger motif," *Nuc. Acids Res.*, 18(9):2715-2720 (1990).

Blaese et al., "Vectors in cancer therapy: how will they deliver?," *Cancer Gene Therapy*, 2(4):291-297 (1995).

Bonde et al., "Ontogeny of the v-erb A Oncoprotein from the Thyroid Hormone Receptor: an Alteration in the DNA Binding Domain Plays a Role Crucial for v-erb A Function," *J. Virology*, 65(4):2037-2046 (1991).

Caponigro et al., "Transdominant genetice analysis of a growth control pathway," *PNAS*, 95:7508-7513 (1998).

Celenza et al., "A Yeast Gene That Is Essential for Release from Glucose Repression Encodes a Protein Kinase," *Science*, 233:1175-1180 (1986).

Cheng et al., "Identification of Potential Target Genes for Adr1p through Characterization of Essential Nucleotides in UAS1," *Mol. Cellular Biol.*, 14(6):3842-3852 (1994).

Cheng et al., "A Single Amino Acid substitution in Zinc Finger 2 of Adr1p Changes its Binding Specificity at two Positions in UAS1," *J. Mol. Biol.*, 251:1-8 (1995).

Choo et al., "A role in DNA binding for the linker sequences of the first three zinc fingers of TFIIIA," *Nuc. Acids Res.*, 21(15):3341-3346 (1993).

Choo et al., "Designing DNA-binding proteins on the surface of filamentous phage," *Curr. Opin. Biotech.*, 6:431-436 (1995).

Choo et al., "Promoter-specific Activation of Gene Expression Directed by Bacteriophage-selected Zinc Fingers," *J. Mol. Biol.*, 273:525-532 (1997).

Choo, Y., "Recognition of DNA methylation by zinc fingers," *Nature Struct. Biol.*, 5(4):264-265 (1998).

Choo et al., "All wrapped up," *Nature Structural Biology*, 5(4):253-255 (1998).

Choo, Y., "End effects in DNA recognition by zinc finger arrays," *Nuc. Acids Res.*, 26(2):554-557 (1998).

Choo et al., "In vivo repression by a site-specific DNA-binding protein designed against an oncogenic sequence," *Nature*, 372:642-645 (1994).

Choo et al., "Physical basis of a protein-DNA recognition code," *Curr. Opin. Struct. Biol.*, 7(1):117-125 (1997).

Choo et al., "Toward a code for the interactions of zinc fingers with DNA: Selection of randomized fingers displayed on phage," *PNAS*, 91:11163-11167 (1994).

Choo et al., "Selection of DNA binding sites for zinc fingers using rationally randomized DNA reveals coded interactions," *PNAS*, 91:11168-11172 (1994).

Corbi, N. et al., "Synthesis of a New Zinc Finger Peptide; Comparison of its 'Code' Deduced and 'CASTing' Derived Binding Sites," *FEBS Letters*, 417: 71-74 (1997).

Crozatier et al., "Single Amino Acid Exchanges in Separate Domains of the *Drosophila serendipity* Zinc finger Protein Cause Embryonic and Sex Biased Lethality," *Genetics*, 131:905-916 (1992).

Debs et al., "Regulation of Gene Expression in Vivo by Liposome-mediated Delivery of a Purified Transcription Factor," *J. Biological Chemistry*, 265(18):10189-10192 (1990).

Desjarlais et al., "Length-encoded multiplex binding site determination: Application to zinc finger proteins," *PNAS*, 91:11099-11103 (1994).

Desjarlais et al., "Use of a zinc-finger consensus sequence framework and specificity rules to design specific DNA binding proteins," *PNAS*, 90:2256-2260 (1993).

Desjarlais et al., "Toward rules relating zinc finger protein sequences and DNA binding site preferences," *PNAS*, 89(16):7345-7349 (1992).

Desjarlais et al., "Redesigning the DNA-Binding Specificity of a Zinc Finger Protein: A Data Base-Guided Approach," *Proteins: Structure, Function, and Genetics*, 12(2):101-104 (1992).

Desjarlais et al., "Redesigning the DNA-Binding Specificity of a Zinc Finger Protein: A Data Base-Guided Approach," *Proteins: Structure, Function, and Genetics*, 13:272 (1992).

Desjardins et al., "Repeated CT Elements Bound by Zinc Finger Proteins Control the Absolute and Relative Activities of the Two Principal Human c-myc Promoters," *Mol. and Cellular Biol.*, 13(9):5710-5724 (1993).

Dibello et al., "The Drosophila Broad-Complex Encodes a Family of Related Proteins Containing Zinc Fingers," *Genetics*, 129:385-397 (1991).

Elrod-Erickson et al., "High-resolution structures of variant Zif268-DNA complexes: implications for understanding zinc finger-DNA recognition," *Structure*, 6(4):451-464 (1998).

Elrod-Erickson et al., "Zif268 protein-DNA complex refined at 1.6 Å: a model system for understanding zinc finger-DNA interactions," *Structure*, 4(10):1171-1180 (1996).

Fairall et al., "The crystal structure of a two zinc-finger peptide reveals an extension to the rules for zinc-finger/DNA recognition," *Nature*, 366:483-487 (1993).

Frankel et al., "Fingering Too Many Proteins," *Cell*, 53:675 (1988).

Friesen et al., "Phage Display of RNA Binding Zinc Fingers from Transcription Factor IIIA," *J. Biological Chem.*, 272(17):10994-10997 (1997).

Ghosh, D., "A relational database of transcription factors," *Nuc. Acids Res.*, 18(7):1749-1756 (1990).

Gogos et al., "Recognition of diverse sequences by class I zinc fingers: Asymmetries and indirect effects on specificity in the interaction between CF2II and A+T-rich sequence elements," *PNAS*, 93(5):2159-2164 (1996).

Gossen et al., "Tight control of gene expression in mammalian cells by tetracycline-responsive promoters," *PNAS*, 89:5547-5551 (1992).

Greisman et al., "A General Strategy for Selecting High-Affinity Zinc Finger Proteins for Diverse DNA Target Sites," *Science*, 275:657-561 (1997).

Hall et al., "Functional Interaction between the Two Zinc finger Domains of the v-erb A Oncoprotein," *Clee Growth & Differentiation*, 3:207-216 (1992).

Hamilton et al., "High affinity binding sites for the Wilms' tumor suppressor protein WT1," *Nuc. Acids Res.*, 23(2):277-284 (1995).

Hamilton et al., "Comparison of the DNA Binding Characteristics of the Related Zinc Finger Proteins WT1 and EGR1," *Biochemistry*, 37:2051-2058 (1998).

Hanas et al., "Internal deletion mutants of *Xenopus* transcription factor IIIA," *Nuc. Acids Res.*, 17(23):9861-9870 (1989).

Hayes et al., "Locations of Contacts between Individual Zinc Fingers of *Xenopus laevis* Transcription Factor IIIA and the Internal Control Region of a 5S RNA Gene," *Biochemistry*, 31:11600-11605 (1992).

Heinzel et al., "A complex containing N-CoR, mSin3 and histone deacetylase mediates transcriptional repression," *Nature*, 387:43-48 (1997).

Hirst et al., "Discrimination of DNA response elements for thyroid hormone and estrogen is dependant on dimerization of receptor DNA binding domains," *PNAS*, 89:5527-5531 (1992).

Hoffman et al., "Structures of DNA-binding mutant zinc finger domains: Implications for DNA binding," *Protein Science*, 2:951-965 (1993).

Isalan et al., "Comprehensive DNA Recognition through Concerted Interactions from Adjacent Zinc Fingers," *Biochemistry*, 37:12026-12033 (1998).

Isalan et al., "Synergy between adjacent zinc fingers in sequence-specific DNA recognition," *PNAS*, 94(11):5617-5621 (1997).

Jacobs, G. H., "Determination of the base recognition positions of zinc fingers from sequence analysis," *EMBO J.*, 11(12):4507-4517 (1992).

Jamieson et al., "A zinc finger directory for high-affinity DNA recognition," *PNAS*, 93:12834-12839 (1996).

Jamieson et al., "In Vitro Selection of Zinc Fingers with Altered DNA-Binding Specificity," *Biochemistry*, 33(19):5689-5695 (1994).

Julian et al., "Replacement of His23 by Cys in a zinc finger of HIV-1 NCp7 led to a change in 1H NMR-derived 3D structure and to a loss of biological activity," *FEBS letters*, 331(1,2):43-48 (1993).

Kamiuchi et al., "New multi zinc finger protein: biosynthetic design and characteristics of DNA recognition," *Nucleic Acids Symposium Series*, 37:153-154 (1997).

Kim et al., "Serine at Position 2 in the DNA Recognition helix of a Cys2-His2 Zinc finger Peptide is Not, in General, Responsible for Base Recognition," *J. Mol. Biol.*, 252:1-5 (1995).

Kim et al., "Site-specific cleavage of DNA-RNA hybrids by zinc finger/FokI cleavage domain fusions," *Gene*, 203:43-49 (1997).

Kim et al., "A 2.2 Å resolution crystal structure of a designed zinc finger protein bound to DNA," *Nat. Struct. Biol.*, 3(11):940-945 (1996).

Kim et al., "Getting a handhold on DNA: Design of poly-zinc finger proteins with femtomolar dissociation constants," *PNAS*, 95:2812-2817 (1998).

Kim et al., "Design of TATA box-binding protein/zinc finger fusions for targeted regulation of gene expression," *PNAS*, 94:3616-3620 (1997).

Kim et al., "Hybrid restriction enzymes: Zinc finger fusions to Fok I cleavage domain," *PNAS*, 93:1156-1160 (1996).

Kim et al., "Transcriptional repression by zinc finger peptides," *J. Biol. Chem.*, 272(47):29795-28000 (1997).

Kinzler et al., "The GLI gene is a member of the Kruppel family of zinc finger proteins," *Nature*, 332:371-4 (1988).

Klug, A., "Gene Regulatory Proteins and Their Interaction with DNA," *Ann. NY Acad. Sci.*, 758:143-160 (1995).

Klug et al., "Protein Motifs 5: Zinc Fingers," *FASEB J.*, 9:597-604 (1995).

Kothekar, V., "Computer simulation of zinc finger motifs from cellular nucleic acid binding protein and their interaction with consensus DNA sequences," *FEBS Letters*, 274(1-2):217-222 (1990).

Kriwacki et al., "Sequence-specific recognition of DNA by zinc-finger peptides derived from the transcription factor Sp1," *PNAS*, 89:9759-9763 (1992).

Krizek et al., "A consensus zinc finger peptide: design, high-affinity metal binding, a pH-dependent structure, and a His to Cys sequence variant," *J. Am. Chem. Soc.*, 113(12):4518-4523 (1991) Abstract.

Kulda et al., "The regulatory gene areA mediating nitrogen metabolite repression in *Aspergillus nidulans*. Mutations affecting specificity of gene activation alter a loop residue of a putative zinc finger," *EMBO J.*, 9(5):1355-1364 (1990).

Liu et al., "Design of polydactyl zinc-finger proteins for unique addressing within complex genomes," *PNAS*, 94(11):5525-5530 (1997).

Loeb et al., "The Sequence of a large L1Md element Reveals a Tandemly Repeated 5' End and Several Features Found in Retrotransposons," *Mol. Cell Biol.*, 6(1):168-182 (1986).

Mandel-Gutfreund et al., "Quantitative parameters for amino acid-base interaction: implications for prediction of protein-DNA binding sites," *Nuc. Acids Res.*, 26(10):2306-2312 (1998).

Margolin et al., "Kruppel-associated boxes are potent transcriptional repression domains," *PNAS*, 91:450-4513 (1994).

Mizushima et al., "pEF-BOS, a powerful mammilian expression vector," *Nuc. Acids Res.*, 18(17):5322 (1990).

Nakagama et al., "Sequence and Structural Requirements for High-Affinity DNA Binding by the WT1 Gene Product," *Molecular and Cellular Biology*, 15(3):1489-1498 (1995).

Nardelli et al., "Zinc finger-DNA recognition: analysis of base specificity by site-directed mutagenesis," *Nuc. Acids Res.*, 20(16):4137-4144 (1992).

Nardelli et al., "Base sequence discrimination by zinc-finger DNA-binding domains," *Nature*, 349:175-178 (1991).

Nekludova et al., "Distinctive DNA conformation with enlarged major groove is found in Zn-finger—DNA and other protein—DNA complexes," *PNAS*, 91:6948-6952 (1994).

Ogata et al., "Solution structure of a DNA-binding unit of Myb: A helix-turn-helix-related motif with conserved tryptophans forming a hydrophobic core," *PNAS*, 89:6428-6432 (1992).

Orkin et al., "Report and Recommendations of the Panel to Assess the NIH Investment in Research on Gene Therapy," Dec. 7, 1995.

Pabo et al., "Systematic Analysis of Possible Hydrogen Bonds between Amino Acid Side Chains and B-form DNA," *J. Biomolecular Struct. Dynamics*, 1:1039-1049 (1983).

Pabo et al., "Protein-DNA Recognition," *Ann. Rev. Biochem.*, 53:293-321 (1984).

Pabo, C. O., "Transcription Factors: Structural Families and Principals of DNA Recognition," *Ann. Rev. Biochem.*, 61:1053-1095 (1992).

Pavletich et al., "Crystal Structure of a Five-Finger GLI-DNA Complex: New Perspectives on Zinc Fingers," *Science*, 261:1701-1707 (1993).

Pavletich et al., "Zinc Finger-DNA Recognition: Crystal Structure of a Zif268-DNA Complex at 2.1 Å," *Science*, 252:809-817 (1991).

Pengue et al., "Repression of transcriptional activity at a distance by the evolutionarily conserved KRAB domain present in a subfamily of zinc finger proteins," *Nuc. Acids Res.*, 22(15):2908-2914 (1994).

Pengue et al., "Transcriptional Silencing of Human Immunodeficiency Virus Type 1 Long Terminal Repeat-Driven Gene Expression by the Kruppel-Associated Box Repressor Domain Targeted to the Transactivating Response Element," *J. Virology*, 69(10):6577-6580 (1995).

Pengue et al., "Kruppel-associated box-mediated repression of RNA polymerase II promoters is influenced by the arrangement of basal promoter elements," *PNAS*, 93:1015-1020 (1996).

Pommerantz et al., "Structure-Based Design of a Dimeric Zinc Finger Protein," *Biochemistry*, 37(4):965-970 (1998).

Pommerantz et al., "Structure-Based Design of Transcription Factors," *Science*, 267:93-96 (1995).

Pommerantz et al., "Analysis of homeodomain function by structure-based design of a transcription factor," *PNAS*, 92:9752-9756 (1995).

Qian et al., "Two-Dimensional NMR Studies of the Zinc Finger Motif: Solution Structures and Dynamics of Mutant ZFY Domains Containing Aromatic Substitutions in the Hydrophobic Core," *Biochemistry*, 31:7463-7476 (1992).

Quigley et al., "Complete Androgen Insensitivity Due to Deletion of Exon C of the Androgen Receptor in Gene Highlights the Functional Importance of the Second Zinc Finger of the Androgen Receptor in Vivo," *Molecular Endocrinology*, 6(7):1103-1112 (1992).

Rauscher et al., "Binding of the Wilms' Tumor Locus Zinc Finger Protein to the EGR-1 Consensus Sequence," *Science*, 250:1259-1262 (1990).

Ray et al., "Repressor to activator switch by mutations in the first Zn finger of the glucocorticoid receptor: Is direct DNA binding necessary?," *PNAS*, 88:7086-7090 (1991).

Rebar et al., "Phage Display Methods for Selecting Zinc Finger Proteins with Novel DNA-Binding Specificities," *Methods in Enzymology*, 267:129-149 (1996).

Rebar et al., "Zinc Finger Phage: Affinity Selection of Fingers with New DNA-Binding Specificities," *Science*, 263:671-673 (1994).

Reith et al., "Cloning of the major histocompatibility complex class II promoter binding protein affected in a hereditary defect in class II gene regulation," *PNAS*, 86:4200-4204 (1989).

Rhodes et al., "Zinc Fingers: They play a key part in regulating the activity of genes in many species, from yeast to humans. Fewer than 10 years ago no one knew they existed," *Scientific American*, 268:56-65 (1993).

Rice et al., "Inhibitors of HIV Nucleocapsid Protein Zinc Fingers as Candidates for the Treatment of AIDS," *Science*, 270:1194-1197 (1995).

Rivera et al., "A humanized system for pharmacologic control of gene expression," *Nature Medicine*, 2(9):1028-1032 (1996).

Rollins et al., "Role of TFIIIA Zinc Fingers In vivo: Analysis of Single-Finger Function in Developing *Xenopus* Embryos," *Molecular Cellular Biology*, 13(8):4776-4783 (1993).

Saleh et al., "A Novel Zinc Finger Gene on Human Chromosome 1qter That Is Alternatively Spliced in Human Tissues and Cell Lines," *Am. J. Hum. Genet.*, 52:192-203 (1993).

Shi et al., "Specific DNA-RNA Hybrid Binding by Zinc Finger Proteins," *Science*, 268:282-284 (1995).

Shi et al., "DNA Unwinding Induced by Zinc Finger Protein Binding," *Biochemistry*, 35:3845-3848 (1996).

Shi et al., "A direct comparison of the properties of natural and designed finger proteins," *Chem. & Biol.*, 2(2):83-89 (1995).

Singh et al., "Molecular Cloning of an Enhancer Binding Protein: Isolation by Screening of an Expression Library with a Recognition Site DNA," *Cell*, 52:415-423 (1988).

Skerka et al., "Coordinate Expression and Distinct DNA-Binding Characteristics of the four EGR-Zinc Finger Proteins in Jukat T Lymphocytes," *Immunobiology*, 198:179-191 (1997).

South et al., "The Nucleocapsid Protein Isolated from HIV-1 Particles Binds Zinc and Forms Retroviral-Type Zinc Fingers," *Biochemistry*, 29:7786-7789 (1990).

Suzuki et al., "Stereochemical basis of DNA recognition by Zn fingers," *Nuc. Acids Res.*, 22(16):3397-3405 (1994).

Suzuki et al. "DNA recognition code of transcription factors in the helix-turn-helix, probe helix, hormone receptor, and zinc finger families," *PNAS*, 91:12357-12361 (1994).

Swirnoff et al., "DNA-Binding Specificity of NGFI-A and Related Zinc Finger Transcription Factors," *Mol. Cell. Biol.*, 15(4):2275-2287 (1995).

Taylor et al, "Designing Zinc-Finer ADR1 Mutants with Altered Specificity of DNA Binding to T in UAS1 Sequences," *Biochemistry*, 34:3222-3230 (1995).

Thiesen et al., "Determination of DNA binding specificities of mutated zinc finger domains," *FEBS Letters*, 283(1):23-26 (1991).

Thiesen et al., "Amino Acid Substitutions in the SP1 Zinc Finger Domain Alter the DNA Binding Affinity to Cognate SP1 Target Site," *Biochem. Biophys. Res. Communications*, 175(1):333-338 (1991).

Thukral et al., "Localization of a Minimal Binding Domain and Activation Regions in Yeast Regulatory Protein ADR1," *Molecular Cellular Biology*, 9(6):2360-2369 (1989).

Thukral et al., "Two Monomers of Yeast Transcription Factor ADR1 Bind a Palindromic Sequence Symmetrically to Activate ADH2 Expression," *Molecular Cellular Biol.*, 11(3):1566-1577 (1991).

Thukral et al., "Alanine scanning site-directed mutagenesis of the zinc fingers of transcription factor ADR1: Residues that contact DNA and that transactivate," *PNAS*, 88:9188-9192 (1991), + correction page.

Thukral et al., "Mutations in the Zinc Fingers of ADR1 That Change the Specificity of DNA Binding and Transactivation," *Mol. Cell Biol.*, 12(6):2784-2792 (1992).

Vortkamp et al., "Identification of Optimized Target Sequences for the GLI3 Zinc Finger Protein," *DNA Cell Biol.*, 14(7):629-634 (1995).

Webster et al., "Conversion of the E1A Cys4 zinc finger to a non-functional His2, Cys2 zinc finger by a single point mutation," *PNAS*, 88:9989-9993 (1991).

Whyatt et al., "The two zinc finger-like domains of GATA-1 have different DNA binding specificities," *EMBO J.*, 12(13):4993-5005 (1993).

Witzgall et al., "The Kruppel-associated box-A (KRAB-A) domain of zinc finger proteins mediates transcriptional repression," *PNAS*, 91:4514-4518 (1994).

Wright et al., "Expression of a Zinc Finger Gene in HTLV-I- and HTLV-II-transformed Cells," *Science*, 248:588-591 (1990).

Wu et al., "Building zinc fingers by selection: Toward a therapeutic application," *PNAS*, 92:344-348 (1995).

Yang et al., "Surface plasmon resonance based kinetic studies of zinc finger-DNA interactions," *J. Immunol. Methods*, 183:175-182 (1995).

Yu et al., "A hairpin ribozyme inhibits expression of diverse strains of human immunodeficiency virus type 1," *PNAS*, 90:6340-6344 (1993).

U.S. Appl. No. 09/424,488, Advisory Action mailed Jan. 28, 2003.
U.S. Appl. No. 09/424,488, Advisory Action mailed Apr. 15, 2003.
U.S. Appl. No. 09/424,488, Examiner Interview Summary mailed Jan. 14, 2003.
U.S. Appl. No. 09/424,488, Examiner Interview Summary mailed Mar. 17, 2003.
U.S. Appl. No. 09/424,488, Examiner Interview Summary mailed Apr. 7, 2003.
U.S. Appl. No. 09/424,488, Examiner Interview Summary mailed May 14, 2003.
U.S. Appl. No. 09/424,488, Notice of Allowance mailed Sep. 30, 2004.
U.S. Appl. No. 09/424,488, Office Action mailed Mar. 28, 2002.
U.S. Appl. No. 09/424,488, Office Action mailed Sep. 9, 2003.
U.S. Appl. No. 09/424,488, Office Action mailed Oct. 1, 2001.
U.S. Appl. No. 09/424,488, Office Action mailed Oct. 22, 2002.
U.S. Appl. No. 10/853,437, Notice of Allowance mailed Mar. 7, 2007.
U.S. Appl. No. 10/853,437, Office Action mailed Oct. 13, 2006.

* cited by examiner

FIG. 1A

```
              8    9   10   11   12   13   14   15   16
Wild-type  5' GTG  GTG  GGC  GCC  GGC  GGT  GTG  GGC  AAG 3'
           3' CAC  CAC  CCG  CGG  CCG  CCA  CAC  CCG  TTG 5'
                                  ↓
EJ mutant  5' GTG  GTG  GGC  GCC  GTC  GGT  GTG  GGC  AAG 3'
           3' CAC  CAC  CCG  CGG  CAG  CCA  CAC  CCG  TTG 5'
```

FIG. 1C

```
       F1  M A E E K P F Q C R I C M R N F S D R S S L T R H T G E K P
       F2              F Q C R I C M R N F S D R S S L T R H T G E K P
       F3              F Q C R I C M R N F S D R S S L T R H T G E K
                                            -1 1 2 3 4 5 6 7 8 9
                        β            β              α-helix
```

NUCLEIC ACID BINDING PROTEINS

The present application is a continuation of U.S. Ser. No. 10/853,437, filed May 24, 2004, now U.S. Pat. No. 7,241,574, which is a continuation of Ser. No. 09/424,488, filed Feb. 24, 2000, now U.S. Pat. No. 6,866,997, which is the U.S. national phase of PCT/GB98/01516 filed May 26, 1998, (each incorporated by reference), which claims priority under 35 USC 119 from GB 9710809.6 filed May 23, 1997.

Protein-nucleic acid recognition is a commonplace phenomenon which is central to a large number of biomolecular control mechanisms which regulate the functioning of eukaryotic and prokaryotic cells. For instance, protein-DNA interactions form the basis of the regulation of gene expression and are thus one of the subjects most widely studied by molecular biologists.

A wealth of biochemical and structural information explains the details of protein-DNA recognition in numerous instances, to the extent that general principles of recognition have emerged. Many DNA-binding proteins contain independently folded domains for the recognition of DNA, and these domains in turn belong to a large number of structural families, such as the leucine zipper, the "helix-turn-helix" and zinc finger families.

Despite the great variety of structural domains the specificity of the interactions observed to date between protein and DNA most often derives from the complementarity of the surfaces of a protein α-helix and the major groove of DNA [Klug, (1993) Gene 135:83-92]. In light of the recurring physical interaction of α-helix and major groove, the tantalising possibility arises that the contacts between particular amino acids and DNA bases could be described by a simple set of rules; in effect a stereochemical recognition code which relates protein primary structure to binding-site sequence preference.

It is clear, however, that no code will be found which can describe DNA recognition by all DNA-binding proteins. The structures of numerous complexes show significant differences in the way that the recognition α-helices of DNA-binding proteins from different structural families interact with the major groove of DNA, thus precluding similarities in patterns of recognition. The majority of known DNA-binding motifs are not particularly versatile, and any codes which might emerge would likely describe binding to a very few related DNA sequences.

Even within each family of DNA-binding proteins, moreover, it has hitherto appeared that the deciphering of a code would be elusive. Due to the complexity of the protein-DNA interaction, there does not appear to be a simple "alphabetic" equivalence between the primary structures of protein and nucleic acid which specifies a direct amino acid to base relationship.

International patent application WO 96/06166 addresses this issue and provides a "syllabic" code which explains protein-DNA interactions for zinc finger nucleic acid binding proteins. A syllabic code is a code which relies on more than one feature of the binding protein to specify binding to a particular base, the features being combinable in the forms of "syllables", or complex instructions, to define each specific contact.

However, this code is incomplete, providing no specific instructions permitting the specific selection of nucleotides other than G in the 5' position of each quadruplet. The method relies on randomisation and subsequent selection in order to generate nucleic acid binding proteins for other specificities. Moreover, this document reports that zinc fingers bind to a nucleic acid triplet or multiples thereof. We have now determined that zinc finger binding sites are determined by overlapping 4 bp subsites, and that sequence-specificity at the boundary between subsites arises from synergy between adjacent fingers. This has important implications for the design and selection of zinc fingers with novel DNA binding specificities.

The present invention provides a more complete code which permits the selection of any nucleic acid sequence as the target sequence, and the design of a specific nucleic acid-binding protein which will bind thereto. Moreover, the invention provides a method by which a zinc finger protein specific for any given nucleic acid sequence may be designed and optimised. The present invention therefore concerns a recognition code which has been elucidated for the interactions of classical zinc fingers with nucleic acid. In this case a pattern of rules is provided which covers binding to all nucleic acid sequences.

According to a first aspect of the present invention, therefore, we provide a method for preparing a nucleic acid binding protein of the Cys2-His2 zinc finger class capable of binding to a nucleic acid quadruplet in a target nucleic acid sequence, wherein binding to base 4 of the quadruplet by an α-helical zinc finger nucleic acid binding motif in the protein is determined as follows:

a) if base 4 in the quadruplet is A, then position +6 in the α-helix is Gln and ++2 is not Asp;
b) if base 4 in the quadruplet is C, then position +6 in the α-helix may be any residue, as long as position ++2 in the α-helix is not Asp.

Preferably, binding to base 4 of the quadruplet by an α-helical zinc finger nucleic acid binding motif in the protein is additionally determined as follows:

c) if base 4 in the quadruplet is G, then position +6 in the α-helix is Arg; or position +6 is Ser or Thr and position ++2 is Asp;
d) if base 4 in the quadruplet is T, then position +6 in the α-helix is Ser or Thr and position ++2 is Asp.

The quadruplets specified in the present invention are overlapping, such that, when read 3' to 5' on the −strand of the nucleic acid, base 4 of the first quadruplet is base 1 of the second, and so on. Accordingly, in the present application, the bases of each quadruplet are referred by number, from 1 to 4, 1 being the 3' base and 4 being the 5' base.

All of the nucleic acid-binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide.

Residues referred to as "++2" are residues present in an adjacent (C-terminal) finger. They reflect the synergistic cooperation between position +2 on base 1 and position +6 of the preceding (N-terminal) finger on base 4 of the preceding (3') quadruplet, which is the same base due to the overlap. Where there is no C-terminal adjacent finger, "++" interactions do not operate.

Cys2-His2 zinc finger binding proteins, as is well known in the art, bind to target nucleic acid sequences via α-helical zinc metal atom co-ordinated binding motifs known as zinc fingers. Each zinc finger in a zinc finger nucleic acid binding protein is responsible for determining binding to a nucleic acid quadruplet in a nucleic acid binding sequence. Preferably, there are 2 or more zinc fingers, for example 2, 3, 4, 5 or 6 zinc fingers, in each binding protein. Advantageously, there are 3 zinc fingers in each zinc finger binding protein.

The method of the present invention allows the production of what are essentially artificial nucleic acid binding proteins.

In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the − strand of the nucleic acid, since it is this strand which is aligned 3' to 5'. These conventions are followed in the nomenclature used herein. It should be noted, however, that in nature certain fingers, such as finger 4 of the protein GLI, bind to the + strand of nucleic acid: see Suzuki et al., (1994) NAR 22:3397-3405 and Pavletich and Pabo, (1993) Science 261:1701-1707. The incorporation of such fingers into nucleic acid binding molecules according to the invention is envisaged.

The invention provides a solution to a problem hitherto unaddressed in the art, by permitting the rational design of polypeptides which will bind nucleic acid quadruplets whose 5' residue is other than G. In particular, the invention provides for the first time a solution for the design of polypeptides for binding quadruplets containing 5' A or C.

Position +6 in the α-helix is generally responsible for the interaction with the base 4 of a given quadruplet in the target. According to the present invention, an A at base 4 interacts with a Glutamine (Gln or Q) at position +6, while a C at base 4 will interact with any amino acid provided that position ++2 is not Aspartic acid (Asp or D).

The present invention concerns a method for preparing nucleic acid binding proteins which are capable of binding nucleic acid. Thus, whilst the solutions provided by the invention will result in a functional nucleic acid binding molecule, it is possible that naturally-occurring zinc finger nucleic acid binding molecules may not follow some or all of the rules provided herein. This does not matter, because the aim of the invention is to permit the design of the nucleic acid binding molecules on the basis of nucleic acid sequence, and not the converse. This is why the rules, in certain instances, provide for a number of possibilities for any given residue. In other instances, alternative residues to those given may be possible. The present invention, thus, does not seek to provide every solution for the design of a binding protein for a given target nucleic acid. It does, however, provide for the first time a complete solution allowing a functional nucleic acid binding protein to be constructed for any given nucleic acid quadruplet.

In a preferred aspect, therefore, the invention provides a method for preparing a nucleic acid binding protein of the Cys2-His2 zinc finger class capable of binding to a nucleic acid quadruplet in a target nucleic acid sequence, wherein binding to each base of the quadruplet by an α-helical zinc finger nucleic acid binding motif in the protein is determined as follows:

a) if base 4 in the quadruplet is G, then position +6 in the α-helix is Arg; or position +6 is Ser or Thr and position ++2 is Asp;
b) if base 4 in the quadruplet is A, then position +6 in the α-helix is Gln and ++2 is not Asp;
c) if base 4 in the quadruplet is T, then position +6 in the α-helix is Ser or Thr and position ++2 is Asp;
d) if base 4 in the quadruplet is C, then position +6 in the α-helix may be any amino acid, provided that position ++2 in the α-helix is not Asp;
e) if base 3 in the quadruplet is G, then position +3 in the α-helix is His;
f) if base 3 in the quadruplet is A, then position +3 in the α-helix is Asn;
g) if base 3 in the quadruplet is T, then position +3 in the α-helix is Ala, Ser or Val; provided that if it is Ala, then one of the residues at −1 or +6 is a small residue;
h) if base 3 in the quadruplet is C, then position +3 in the α-helix is Ser, Asp, Glu, Leu, Thr or Val;
i) if base 2 in the quadruplet is G, then position −1 in the α-helix is Arg;
j) if base 2 in the quadruplet is A, then position −1 in the α-helix is Gln;
k) if base 2 in the quadruplet is T, then position −1 in the α-helix is Asn or Gln;
l) if base 2 in the quadruplet is C, then position −1 in the α-helix is Asp;
m) if base 1 in the quadruplet is G, then position +2 is Asp;
n) if base 1 in the quadruplet is A, then position +2 is not Asp;
o) if base 1 in the quadruplet is C, then position +2 is not Asp;
p) if base 1 in the quadruplet is T, then position +2 is Ser or Thr.

The foregoing represents a set of rules which permits the design of a zinc finger binding protein specific for any given nucleic acid sequence. A novel finding related thereto is that position +2 in the helix is responsible for determining the binding to base 1 of the quadruplet. In doing so, it cooperates synergistically with position +6, which determines binding at base 4 in the quadruplet, bases 1 and 4 being overlapping in adjacent quadruplets.

A zinc finger binding motif is a structure well known to those in the art and defined in, for example, Miller et al., (1985) EMBO J. 4:1609-1614; Berg (1988) PNAS (USA) 85:99-102; Lee et al., (1989) Science 245:635-637; see International patent applications WO 96/06166 and WO 96/32475, corresponding to U.S. Ser. No. 08/422,107, incorporated herein by reference.

As used herein, "nucleic acid" refers to both RNA and DNA, constructed from natural nucleic acid bases or synthetic bases, or mixtures thereof. Preferably, however, the binding proteins of the invention are DNA binding proteins.

In general, a preferred zinc finger framework has the structure (SEQ ID NO: 24):

(A)

Where X is any amino acid, and the numbers in subscript indicate the possible numbers of residues represented by X.

In a preferred aspect of the present invention, zinc finger nucleic acid binding motifs may be represented as motifs having the following primary structure (SEQ ID NO:3):

(B)

−1 1 2 3 4 5 6 7 8 9 wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together coordinate the zinc metal atom, are marked in bold text and are usually invariant, as is the Leu residue at position +4 in the α-helix.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518-4523) and that Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix co-ordinated by a zinc atom which contacts four Cys or His residues, does not alter. As used herein, structures (A) and (B) above are taken as an exemplary structure representing all zinc finger structures of the Cys2-His2 type.

Preferably, $X^a$ is F/Y-X or P-F/Y-X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I.

Preferably, $X^c$ is S or T.

Preferably, $X_{2-3}$ is G-K-A, G-K-C, G-K-S or G-K-G. However, departures from the preferred residues are possible, for example in the form of M-R-N or M-R.

Preferably, the linker is T-G-E-K (SEQ ID NO:4) or T-G-E-K-P (SEQ ID NO:5).

As set out above, the major binding interactions occur with amino acids −1, +2, +2, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr.

In a most preferred aspect, therefore, bringing together the above, the invention allows the definition of every residue in a zinc finger nucleic acid binding motif which will bind specifically to a given nucleic acid quadruplet.

The code provided by the present invention is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target nucleic acid quadruplet.

Preferably, however, the number of possibilities may be significantly reduced. For example, the non-critical residues +1, +5 and +8 may be occupied by the residues Lys, Thr and Gln respectively as a default option. In the case of the other choices, for example, the first-given option may be employed as a default. Thus, the code according to the present invention allows the design of a single, defined polypeptide (a "default" polypeptide) which will bind to its target quadruplet.

In a further aspect of the present invention, there is provided a method for preparing a nucleic acid binding protein of the Cys2-His2 zinc finger class capable of binding to a target nucleic acid sequence, comprising the steps of:

a) selecting a model zinc finger domain from the group consisting of naturally occurring zinc fingers and consensus zinc fingers; and b) mutating one or more of positions −1, +2, +3 and +6 of the finger as required according to the rules set forth above.

In general, naturally occurring zinc fingers may be selected from those fingers for which the nucleic acid binding specificity is known. For example, these may be the fingers for which a crystal structure has been resolved: namely Zif 268 (Elrod-Erickson et al., (1996) Structure 4:1171-1180), GLI (Pavletich and Pabo, (1993) Science 261:1701-1707), Tramtrack (Fairall et al., (1993) Nature 366:483-487) and YY1 (Houbaviy et al., (1996) PNAS (USA) 93:13577-13582).

The naturally occurring zinc finger 2 in Zif 268 makes an excellent starting point from which to engineer a zinc finger and is preferred.

Consensus zinc finger structures may be prepared by comparing the sequences of known zinc fingers, irrespective of whether their binding domain is known. Preferably, the consensus structure is selected from the group consisting of the consensus structure P Y K C P E C G K S F S Q K S D L V K H Q R T H T G (SEQ ID NO:6), and the consensus structure P Y K C S E C G K A F S Q K S N L T R H Q R I H T G E K P (SEQ ID NO:7).

The consensuses are derived from the consensus provided by Krizek et al. (1991) J. Am. Chem. Soc. 113:4518-4523 and from Jacobs, (1993) PhD thesis, University of Cambridge, UK. In both cases, the linker sequences described above for joining two zinc finger motifs together, namely TGEK (SEQ ID NO:4) or TGEKP (SEQ ID NO:5) can be formed on the ends of the consensus. Thus, a P may be removed where necessary, or, in the case of the consensus terminating T G, E K (P) (SEQ ID NOS:4 and 5) can be added.

When the nucleic acid specificity of the model finger selected is known, the mutation of the finger in order to modify its specificity to bind to the target nucleic acid may be directed to residues known to affect binding to bases at which the natural and desired targets differ. Otherwise, mutation of the model fingers should be concentrated upon residues −1, +2, +3 and +6 as provided for in the foregoing rules.

In order to produce a binding protein having improved binding, moreover, the rules provided by the present invention may be supplemented by physical or virtual modelling of the protein/nucleic acid interface in order to assist in residue selection.

Zinc finger binding motifs designed according to the invention may be combined into nucleic acid binding proteins having a multiplicity of zinc fingers. Preferably, the proteins have at least two zinc fingers. In nature, zinc finger binding proteins commonly have at least three zinc fingers, although two-zinc finger proteins such as Tramtrack are known. The presence of at least three zinc fingers is preferred. Binding proteins may be constructed by joining the required fingers end to end, N-terminus to C-terminus. Preferably, this is effected by joining together the relevant nucleic acid coding sequences encoding the zinc fingers to produce a composite coding sequence encoding the entire binding protein. The invention therefore provides a method for producing a nucleic acid binding protein as defined above, wherein the nucleic acid binding protein is constructed by recombinant DNA technology, the method comprising the steps of:

a) preparing a nucleic acid coding sequence encoding two or more zinc finger binding motifs as defined above, placed N-terminus to C-terminus;

b) inserting the nucleic acid sequence into a suitable expression vector; and c) expressing the nucleic acid sequence in a host organism in order to obtain the nucleic acid binding protein.

A "leader" peptide may be added to the N-terminal finger. Preferably, the leader peptide is MAEEKP (SEC) ID NO:8).

The nucleic acid encoding the nucleic acid binding protein according to the invention can be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2μ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA encoding the nucleic acid binding protein is more complex than that of exogenously replicated vector because restriction enzyme digestion is required to excise nucleic acid binding protein DNA. DNA an be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up nucleic acid binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the nucleic acid binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to nucleic acid binding protein encoding nucleic acid. Such a promoter may be inducible or constitutive. The promoters are operably linked to DNA encoding the nucleic acid binding protein by removing the promoter from the source DNA by restriction enzyme digestion and inserting the isolated promoter sequence into the vector. Both the native nucleic acid binding protein promoter sequence and many heterologous promoters may be used to direct amplification and/or expression of nucleic acid binding protein encoding DNA.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding nucleic acid binding protein, using linkers or adapters to supply any required restriction sites. Promoters for use in bacterial systems will also generally contain a Shine-Delgarno sequence operably linked to the DNA encoding the nucleic acid binding protein.

Preferred expression vectors are bacterial expression vectors which comprise a promoter of a bacteriophage such as phageχ or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60-89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phase by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpress™ (Invitrogen) or pTrc99 (Pharmacia Biotech SE) or vectors containing the tac promoter such as pKK223-3 (Pharmacia Biotech) or PMAL (New England Biolabs, Mass. USA).

Moreover, the nucleic acid binding protein gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Nucleic acid binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with nucleic acid binding protein sequence, provided such promoters are compatible with the host cell systems.

Transcription of a DNA encoding nucleic acid binding protein by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to nucleic acid binding protein DNA, but is preferably located at a site 5' from the promoter.

Advantageously, a eukaryotic expression vector encoding a nucleic acid binding protein according to the invention may comprise a locus control region (LCR). LCRs are capable of directing high-level integration site independent expression of transgenes integrated into host cell chromatin, which is of importance especially where the nucleic acid binding protein gene is to be expressed in the context of a permanently-transfected eukaryotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding nucleic acid binding protein.

An expression vector includes any vector capable of expressing nucleic acid binding protein nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding nucleic acid binding protein may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding nucleic acid binding protein in mammalian cells. Transient expression usually involves the use of an expression vector that is able to replicate efficiently in a host cell, such that the host cell accumulates many copies of the expression vector, and, in turn, synthesises high levels of nucleic acid binding protein. For the purposes of the present invention, transient expression systems are useful e.g. for identifying nucleic acid binding protein mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing nucleic acid binding protein expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokarvote, yeast and higher eukaryote cells may be used for replicating DNA and producing the nucleic acid binding protein. Suitable prokaryotes include eubacteria, such as Gram-negative or Gram-positive organisms, such as *E. coli*, e.g. *E. coli* K-12 strains. DH5a and HB101, or *Bacilli*. Further hosts suitable for the nucleic acid binding protein encoding vectors include eukaryotic microbes such as filamentous fungi or yeast, e.g. *Saccharomyces cerevisiae*. Higher eukaryotic cells include insect and vertebrate cells, particularly mammalian cells including human cells or nucleated cells from other mulicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of the nucleic acid binding protein-encoding nucleic acid to form the nucleic acid binding protein. The precise amounts of DNA encoding the nucleic acid binding protein may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition. Cold Spring Harbor Laboratory Press).

Transfected or transformed cells are cultured using media and culturing methods known in the art, preferably under conditions, whereby the nucleic acid binding protein encoded by the DNA is expressed. The composition of suitable media is known to those in the art, so that they can be readily prepared. Suitable culturing media are also commercially available.

In a further aspect, the invention also provides means by which the binding of the protein designed according to the rules can be improved by randomising the proteins and selecting for improved binding. In this aspect, the present invention represents an improvement of the method set forth in WO 96/06166. Thus, zinc finger molecules designed according to the invention may be subjected to limited randomisation and subsequent selection, such as by phage display, in order to optimise the binding characteristics of the molecule.

Preferably, therefore, the method according to the invention comprises the further steps of randomising the sequence of the zinc finger binding motifs at selected sites, screening the randomised molecules obtained and selecting the molecules having the most advantageous properties. Generally, those molecules showing higher affinity and/or specificity of the target nucleic acid sequence are selected.

Mutagenesis and screening of target nucleic acid molecules may be achieved by any suitable means. Preferably, the mutagenesis is performed at the nucleic acid level, for example by synthesising novel genes encoding mutant proteins and expressing these to obtain a variety of different proteins. Alternatively, existing genes can be themselves mutated, such by site-directed or random mutagenesis, in order to obtain the desired mutant genes.

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis. D. H. Gelfand, J. J. Sninsky, T. J. White (eds.). Academic Press, New York, 1990). Preferably, the commercially available Altered Site II Mutagenesis System (Promega) may be employed, according to the directions given by the manufacturer.

Screening of the proteins produced by mutant genes is preferably performed by expressing the genes and assaying the binding ability of the protein product. A simple and advantageously rapid method by which this may be accomplished is by phage display, in which the mutant polypeptides are expressed as fusion proteins with the coat proteins of filamentous bacteriophage, such as the minor coat protein pII of bacteriophage m13 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) Current Opinions in Biotechnology 6:431-436; Smith, (1985) Science 228:1315-1317; and McCafferty et al., (1990) Nature 348:552-554; all incorporated herein by reference. Vector systems and kits for phage display are available commercially, for example from Pharmacia.

Randomisation of the zinc finger binding motifs produced according to the invention is preferably directed to those residues where the code provided herein gives a choice of residues. For example, therefore, positions +1, +5 and +8 are advantageously randomised, whilst preferably avoiding hydrophobic amino acids; positions involved in binding to the nucleic acid, notably −1, +2, +3 and +6, may be randomised also, preferably within the choices provided by the rules of the present invention.

Preferably, therefore, the "default" protein produced according to the rules provided by the invention can be improved by subjecting the protein to one or more rounds of randomisation and selection within the specified parameters.

nucleic acid binding proteins according to the invention may be employed in a wide variety of applications, including diagnostics and as research tools. Advantageously, they may be employed as diagnostic tools for identifying the presence of nucleic acid molecules in a complex mixture. nucleic acid binding molecules according to the invention can differentiate single base pair changes in target nucleic acid molecules.

Accordingly, the invention provides a method for determining the presence of a target nucleic acid molecule, comprising the steps of:
a) preparing a nucleic acid binding protein by the method set forth above which is specific for the target nucleic acid molecule;
b) exposing a test system comprising the target nucleic acid molecule to the nucleic acid binding protein under conditions which promote binding, and removing any nucleic acid binding protein which remains unbound;
c) detecting the presence of the nucleic acid binding protein in the test system.

In a preferred embodiment, the nucleic acid binding molecules of the invention can be incorporated into an ELISA assay. For example, phage displaying the molecules of the invention can be used to detect the presence of the target nucleic acid, and visualised using enzyme-linked anti-phage antibodies.

Further improvements to the use of zinc finger phage for diagnosis can be made, for example, by co-expressing a marker protein fused to the minor coat protein (gVIII) of bacteriophage. Since detection with an anti-phage antibody would then be obsolete, the time and cost of each diagnosis would be further reduced. Depending on the requirements, suitable markers for display might include the fluorescent proteins (A. B. Cubitt, et al., (1995) *Trends Biochem Sci.* 20, 448-455; T. T. Yang, et al., (1996) *Gene* 173, 19-23), or an enzyme such as alkaline phosphatase which has been previously displayed on gIII (J. McCafferty, R. H. Jackson, D. J. Chiswell, (1991) *Protein Engineering* 4, 955-961) Labelling different types of diagnostic phage with distinct markers would allow multiplex screening of a single nucleic acid sample. Nevertheless, even in the absence of such refinements, the basic ELISA technique is reliable, fast, simple and particularly inexpensive. Moreover it requires no specialised apparatus, nor does it employ hazardous reagents such as radioactive isotopes, making it amenable to routine use in the clinic. The major advantage of the protocol is that it obviates the requirement for gel electrophoresis, and so opens the way to automated nucleic acid diagnosis.

The invention provides nucleic acid binding proteins which can be engineered with exquisite specificity. The invention lends itself, therefore, to the design of any molecule of which specific nucleic acid binding is required. For example, the proteins according to the invention may be employed in the manufacture of chimeric restriction enzymes, in which a nucleic acid cleaving domain is fused to a nucleic acid binding domain comprising a zinc finger as described herein.

Figure 2:
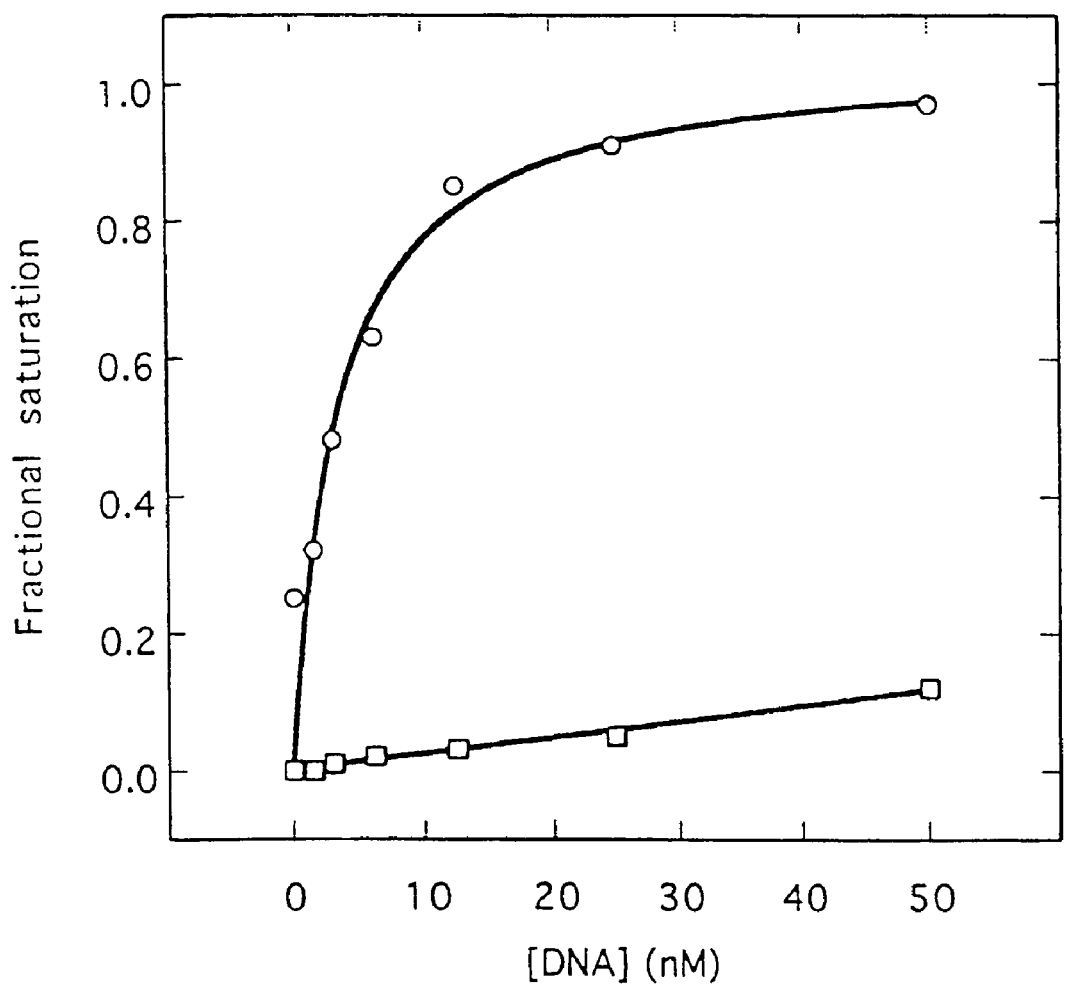
Figure 3:
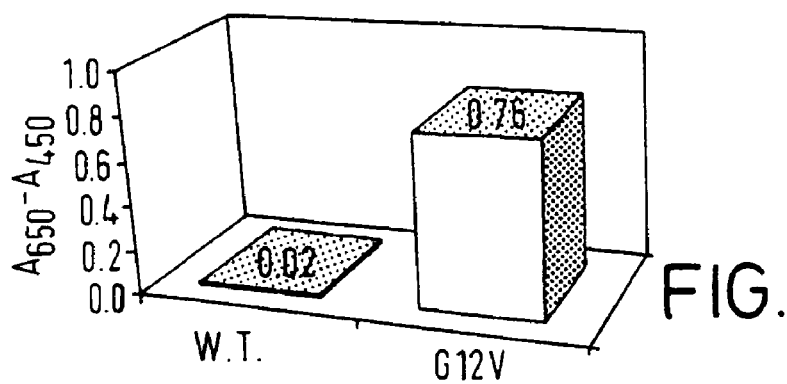
Figure 4:
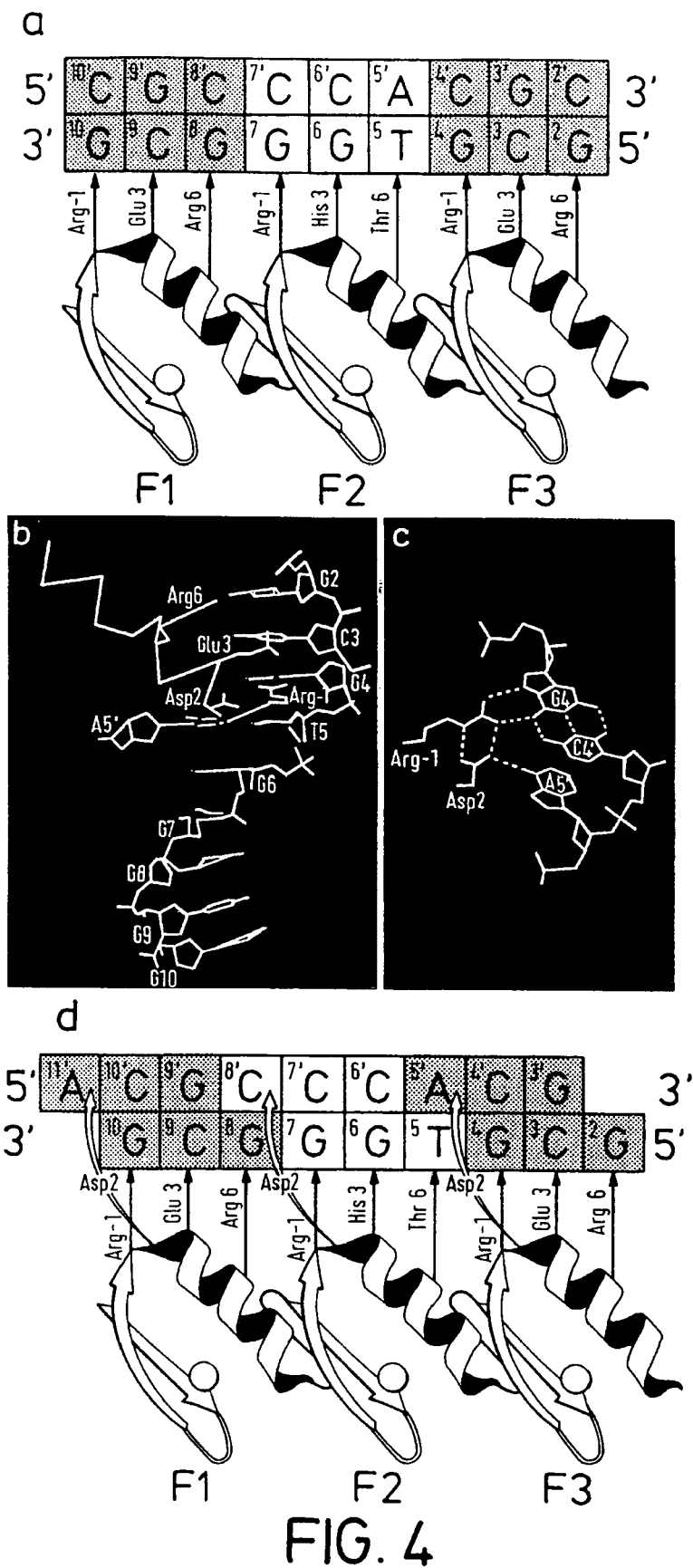
Figure 5:
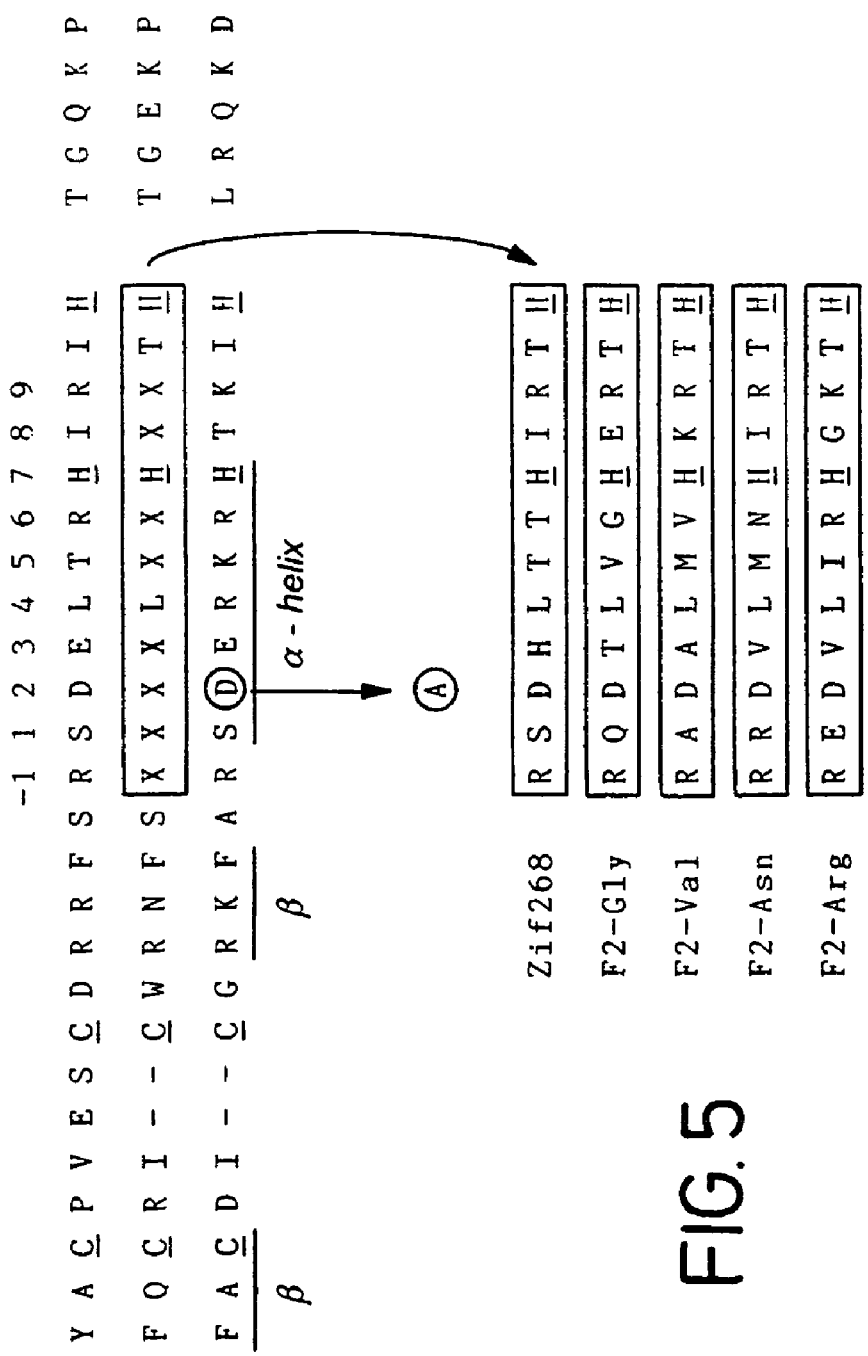

The invention is described below, for the purpose of illustration only, in the following examples, with reference to the figures, in which:

FIGS. 1A, B, and C (SEQ ID NOS:12, 13, 14, 9 and 15, in order of appearance) illustrate the design of a zinc finger binding protein specific (C) for a G12V mutant ras oncogene (A) and interaction of the zinc finger protein with the target site (B);

FIG. 2 illustrates the binding specificity of the binding protein for the oncogene as opposed to the wild-type ras sequence; and FIG. 3 illustrates the results of an ELISA assay performed using the anti-ras binding protein with both wild-type and mutant target nucleic acid sequences;

FIG. 4 illustrates interactions between the Zif268 DNA-binding domain and DNA. (a) Schematic diagram of modular recognition between the three zinc fingers of Zif268 and triplet subsites of an optimised DNA binding site. Straight arrows indicate the stereochemical juxtapostioning of recognition residues with bases of the contacted G-rich DNA strand. Note that since the N-terminal finger contacts the 3' end of the DNA and the C-terminal finger the 5' end, binding to the G-rich strand is said to be antiparallel. (b) View of Zif268 finger 3 bound to DNA, showing the possibility of interaction with both DNA strands. Co-ordinates from Pavletich & Pabo, (1991) Science 252:809-817. (c) The potential hydrogen bonding network between bases on both strands of the DNA and positions −1 (Arg) and 2 (Asp) of finger 3 (Pavletich & Pabo 1991). (d) Schematic diagram of recognition between the three zinc fingers of Zif268 and an optimised DNA binding site including 'cross-strand' interactions. Recognition contacts between Asp2 of each finger and the parallel DNA strand (shown by curly arrows) mean that each finger binds overlapping, 4 bp subsites:

FIG. 5 (SEQ ID NOS: 16-23, in order of appearance) shows the amino acid sequences of the three finger constructs used in this study, including wild-type Zif268 and four variants selected from a phage display library in which finger 2 is randomized. Boxed regions indicate the varied regions in each construct. The conserved zinc chelating residues of the zinc fingers are underlined. The aspartate in position 2 of finger 3 and the alanine to which it is mutated in this study are both circled;

FIGS. 6A-E (portions of SEQ ID NOS: 19-23 in order of appearance) show the binding site signatures of the middle finger before and after alanine mutagenesis in position 2 of finger 3. The ELISA signal ($A_{450}$-$A_{650}$) showing interaction of zinc finger phage with each of five (A-E) positionally randomized DNA library plotted vertically. From the pattern of binding to these libraries, one or a small number of binding sites can be read off and these are written on the right of the figure. Mutagenesis of position 2 in finger 3 can change the binding specificity for the middle triplet of the Zif268 binding site. In such cases, changes are noted for base 5, but not bases 6 and 7 of the DNA binding site (see FIG. 4A); and FIGS. 7A and B depict the apparent equilibrium binding curves showing the effect of replacing Asp2 in finger 3 by Ala for (A) Zif268 DNA-binding domain (consensus binding site used: 5'-GCG TGG GCG-3'); and (B) F2-Arg construct (consensus binding site used: 5'-GCG GTG GCG-3'). Wild-type and mutant constructs are denoted by 'wt' and 'mut' respectively.

EXAMPLE 1

Construction of a Zinc Finger Protein

The target selected for the zinc finger nucleic acid binding protein is the activating point mutation of the human EJ bladder carcinoma ras oncogene, which was the first DNA lesion reported to confer transforming properties on a cellular proto-oncogene. Since the original discovery, ras gene mutations have been found to occur at high frequencies in a variety of human cancers and are established targets for the diagnosis of oncogenesis at early stages of tumour growth.

The EJ bladder carcinoma mutation is a single nucleotide change in codon 12 of H-ras, which results in a mutation from GGC to GTC at this position. A zinc finger peptide is designed to bind a 10 bp DNA site assigned in the noncoding strand of the mutant ras gene, such that three fingers contact 'anticodons' 10, 11 and 12 in series, as shown in FIG. 1, plus the 5' preceding G (on the +strand of the DNA). The rationale of this assignment takes into account the fact that zinc fingers make most contacts to one DNA strand, and the mutant noncoding strand carries an adenine which can be strongly discriminated from the cytosine present in the wild-type ras, by a bidentate contact from an asparagine residue.

The first finger of the designer lead peptide is designed according to the rules set forth herein starting from a Zif268 finger 2 model to bind the quadruplet 5'-GCCG-3', which corresponds to 'anticodon' 10 of the designated binding site plus one 3' base. The finger has the following sequence:

FQCRICMRNFSDRSSLTRHTRTHTGEKP    (SEQ ID NO:9)

-1 1 2 3 4 5 6 7 8 9

A DNA coding sequence encoding this polypeptide is constructed from synthesised oligonucleotides.

Given the similarity of the DNA subsites, the second and third fingers of the DNA-binding domain are direct repeats of this first finger, but in which the third α-helical residue which contacts base 3 of a quadruplet, +3, is mutated according to recognition rules, to histidine in finger 2 and asparagines in finger 3, such that the specificity of these fingers is predicted to be 5'-GGCG-3' (includes 'anticodon' 11) and 5'-GACG-3' (includes 'anticodon' 12) respectively. Thus, the second and third finger polypeptides have the sequences

FQCRICMRNFSDRSHLTRHTRTHTGEKP    (SEQ ID NO:10)

and

FQCRICMRNFSDRSNLTRHTRTHTGEK    (SEQ ID NO:11)

respectively.

A construct consisting of DNA sequences encoding the three fingers joined together, preceded by a leader MAEEKP at the N-terminus, is cloned as a fusion to the minor coat protein (gene III) of bacteriophage Fd in the phage vector Fd-Tet-SN (Y. Choo, A. Klug, (1994) *Proc. Natl. Acad. Sci. U.S.A.* 91, 11163-11167). In phage display screening, the DNA-binding domain is able to bind the mutated ras sequence with an apparent $K_d$ of 17 nM, and to discriminate strongly against the wild-type sequence.

EXAMPLE 2

Improvement of Binding Performance by Selective Randomisation

While a $K_d$ of 17 nM is sufficient for most practical applications of DNA-binding proteins, the apparent affinity of the designed protein falls about 5-fold short of the $K_d$s in the nanomolar range which are found for the reaction of wild-type zinc finger proteins with their natural binding sites (Y. Choo, A. Klug, (1994) *Proc. Natl. Acad. Sci. U.S.A.* 91, 11168-11172).

According to the recognition rules, the first finger of the lead peptide could contact cytosine using one of Asp, Glu, Ser or Thr in the third α-helix position. To determine the optimal contact, the codon for helical position 3 of finger 1 is engineered by cassette mutagenesis to have position 1=A/G, position 2=A/C/G and position 3=C/G. Therefore in addition to Asp, Glu, Ser and Thr, the randomisation also specifies Ala, Arg, Asn, Gly and Lys. Selections from this mini-library are over one round of phage binding to 5 nM mutant DNA oligo in 100 μl PBS containing 50 μM ZnCl$_2$, 2% (w/v) fat-free dried milk (Marvel) and 1% (v/v) Tween®-20 detergent, with 1 μg poly dIdC as competitor, followed by six washes with PBS containing 50 μM ZnCl$_2$ and 1% (v/v) Tween®-20 detergent. Bound phage are eluted with 0.1M triethylamine for 3 mins, and immediately transferred to an equal volume of 1M Tris-Cl pH 7.4.

A single round of randomisation and selection is found to be sufficient to improve the affinity of the lead zinc finger peptide to this standard. A small library of mutants is constructed with limited variations specifically in the third α-helical position (+3) of finger 1 of the designed peptide. Selection from this library yields an optimised DNA-binding domain with asparagine at the variable position, which is able to bind the mutant ras sequence with an apparent $K_d$ of 3 nM, i.e. equal to that of the wild-type Zif268 DNA-binding domain (FIG. 2). The selection of asparagine at this position to bind opposite a cytosine is an unexpected deviation from the recognition rules, which normally pair asparagine with adenine.

The selection of asparagine is, however, consistent with physical considerations of the protein-DNA interface. In addition to the classical bidentate interaction of asparagine and adenine observed in zinc finger-DNA complexes, asparagine has been observed to bridge a base-pair step in the major groove of DNA, for example in the co-crystal structures of the GCN4 DNA-binding domain. A number of different base-pair steps provide the correct stereochemical pairings of hydrogen bond donors and acceptors which could satisfy asparagine, including the underlined step G<u>CC</u> of ras 'anticodon' 10. Although asparagine in position 3 of the zinc finger helix would not normally be positioned to bridge a base-pair step according to the Zif268 model, it is known that a bend in DNA can give scope to non-canonical zinc finger-DNA interactions (L. Fairall, J. W. R. Schwabe, L. Chapman. J. T. Finch, D. Rhodes, (1993) *Nature* 366, 483-487). The sequence GGC (codon 10) is frequently found on the outside of a bend in the nucleosome core, and has been observed to confer an intrinsic bend in the crystal structure of a decameric DNA oligonucleotide. In the latter case, the bend arises from preferential stacking of the purines this is associated with a large propeller twist and narrowing of the major groove, both of which would favour bridging of the base-pair step by asparagine (T. E. Ellenberger, C. J. Brandl, K. Struhl, S. C. Harrison, (1992) *Cell* 71, 1223-1237). Therefore, in addition to explaining the selection of the non-canonical contact in the optimised complex, the sequence-dependent deformation of ras DNA could account for our observation that wild-type and EJ ras gene fragments have different electrophoretic mobility in polyacrylamide gels, since the wild-type ras gene has two GGC sequences 5 bp apart and hence out of helical phase (resulting in no net bend), while the EJ mutation affects one of these GGC sequences.

Thus, while it is possible to engineer an adequate DNA-binding domain by rational design based on recognition rules, the binding affinity of this lead peptide is improved using phage display leading to the selection of a non-canonical DNA contact.

EXAMPLE 3

Diagnosis of a Ras Mutation Using the Zinc Finger Nucleic Acid Binding Protein

The optimised DNA-binding domain displayed on phage is applied in the diagnosis of the activating point mutation of the EJ ras oncogene. Bacterial culture supernatant containing the diagnostic phage is diluted 1:1 with PBS containing 50 μM ZnCl$_2$, 4% (w/v) fat-free dried milk (Marvel) and 2% (v/v) Tween®-20 detergent. Biotinylated oligonucleotides (7.5 pmol) containing double stranded DNA comprising codons 8-16 from the wild type or the point-mutated ras gene are added to 50 μl of the diluted phage and incubated for 1 h at 20° C. In the experiment shown in FIG. 3, bound phage are captured with 0.5 mg streptavidin coated paramagnetic beads (Dynal)—however streptavidin coated microtitre plates (Boehringer Mannheim) can also be used without alteration to the protocol. Unbound phage are removed by washing the beads 6 times with PBS containing 50 µM $ZnCl_2$ and 1% (v/v) Tween®-20 detergent. The beads are subsequently incubated for 1 h at RT with anti-M13 IgG conjugated to horseradish peroxidase (Pharmacia Biotech) diluted 1:5000 in PBS containing 50 µM $ZnCl_2$ and 2% (w/v) fat-free dried milk (Marvel). Excess antibody is removed by washing 6 times with PBS containing 50 µM $ZnCl_2$ and 0.05% (v/v) Tween®-20 detergent, and 3 times with PBS containing 50 µM $ZnCl_2$. The ELISA is developed with 0.1 mg/ml tetramethylbenzidine (Sigma) in 0.1M sodium acetate pH5.4 containing 2 µl of fresh 30% hydrogen peroxide per 10 ml buffer, and after approximately 1 min, stopped with an equal volume of 2M $H_2SO_4$. The reaction produces a yellow colour which is quantitated by subtracting the absorbance at 650 nm from the absorbance at 450 nm. It should be noted that in this protocol the ELISA is not made competitive, however, soluble (non biotinylated) wild-type ras DNA could be included in the binding reactions, possibly leading to higher discrimination between wild-type and mutant ras.

Phage are retained specifically by DNA bearing the mutant, but not the wild-type ras sequence, allowing the detection of the point mutation by ELISA (FIG. 3).

EXAMPLE 4

Design of an Anti-HIV Zinc Finger

The sequence of the HIV TAR, the region of the LTR which is responsible for transactivation by Tat, is known (Jones and Peterlin, (1994) Ann. Rev. Biochem. 63:717-743). A sequence with the TAT region is identified and a zinc finger polypeptide designed to bind thereto.

The selected sequence is 5'-AGA GAG CTC-3', which is the complement of nucleotides +34 to +42 of HIV. The corresponding amino acids required in fingers 1, 2 and 3 of a zinc finger binding protein are determined according to the rules set forth above, as follows:

Finger 3:
target 5'-AGA-3'
Position −1 Gln
Position +2 Gly
Position +3 His
Position +6 Val
Finger 2:
target 5'-GAG-3'
Position −1 Arg
Position +2 Ser
Position +3 Asn
Position +6 Arg
Finger 1
target 5'-CTC-3'
Position −1 Asp
Position +3 Ser
Position +6 Glu The framework of the polypeptide is taken from the Zif268 middle finger. The sequence of the entire polypeptide is shown in SEQ. ID. No. 2.

Residues +2 and +6 of finger 3 are partially selected by randomisation and phage display selection. At position 2, two triplets are used, GAT and GGT, coding for Asp or Gly. Position +6 was randomised. In these positions, the residues Gly and Val are selected. The methodology employed is as follows: colony PCR is performed with one primer containing a single mismatch to create the required randomisations in finger 3. Cloning of PCR product in phage vector is as described previously (Choo, Y. & Klug, A. (1994) Proc. Natl. Acad. Sci. USA 91, 11163-11167; Choo, Y. & Klug, A. (1994) Proc. Natl. Acad. Sci. USA 91, 11168-11172). Briefly, forward and backward PCR primers contained unique restriction sites for Not I or Sfi I respectively and amplified an approximately 300 base pair region encompassing three zinc fingers. PCR products are digested with Sfi I and Not I to create cohesive ends and are ligated to 100 ng of similarly digested fd-Tet-SN vector. Electrocompetent TG1 cells are transformed with the recombinant vector. Single colonies of tranformants are grown overnight in 2×TY containing 50 µM $ZnCl_2$ 15 µg/ml tetracycline. Single stranded DNA is prepared from phage in the culture supernatant and sequenced with Sequenase 2.0 (United States Biochemical).

The polypeptide designed according to the invention is then tested for binding to HIV DNA and positive results are obtained.

EXAMPLE 5

Alanine mutagenesis of the Asp2 in finger 3 is carried out on the wild-type Zif268 DNA-binding domain and four related peptides isolated from the phage display library as follows (see also FIG. 5):

*E. coli* TG1 cells are tranfected with fd phage displaying zinc fingers. Colony PCR is performed with one primer containing a single mismatch to create the Asp to Ala change in finger 3. Cloning of PCR product in phage vector is as described previously (Choo, Y. & Klug, A. (1994) Proc. Natl. Acad. Sci. USA 91, 11163-11167; Choo, Y. & Klug, A. (1994) Proc. Natl. Acad. Sci. USA 91, 11168-11172). Briefly, forward and backward PCR primers contained unique restriction sites for Not I or Sfi I respectively and amplified an approximately 300 base pair region encompassing three zinc fingers. PCR products are digested with Sfi I and Not I to create cohesive ends and are ligated to 100 ng of similarly digested fd-Tet-SN vector. Electrocompetent TG1 cells are transformed with the recombinant vector. Single colonies of tranformants are grown overnight in 2×TY containing 50 µM $ZnCl_2$ 15 µg/ml tetracycline. Single stranded DNA is prepared from phage in the culture supernatant and sequenced with Sequenase 2.0 (United States Biochemical).

The peptides are chosen for this experiment on the basis of the identity of the residue at position 6 of the middle finger. Peptide F2-Arg, which contains Arg at position 6 of finger 2, is chosen since it should specify 5'-G in the 'middle' cognate triplet regardless of the mutation. On the other hand. the peptide F2-Gly with Gly at position 6 would be expected to lose all specificity at the 5' position of the 'middle' triplet following alanine mutagenesis in finger 3. The other two peptides analysed, F2-Val and F2-Asn, with Val and Asn at position 6 respectively, are chosen because these particular residues might confer some alternative binding specificity after the constraint imposed by position 2 in finger 3 is removed by alanine mutagenesis (Seeman, N. D., Rosenberg, J. M. & Rich. A. (1976) Proc. Nat. Acad. Sci. USA 73, 804-808; Suzuki, M (1994) Structure 2, 317-326).

The DNA binding specificity of each middle finger is assessed before and after the alanine mutation in finger 3 by the 'binding site signature' method (Choo and Kug, 1994). This procedure involves screening each zinc finger phage for binding to 12 DNA libraries, each based on the DNA binding site of Zif768 but containing one fixed and two randomised nucleotide positions in the 'middle' triplet. Each of the possible 64 'middle' triplets is present in a unique combination of three of these positionally randomised libraries; for example the triplet GAT would be found in the GNN, NAN and NNT libraries only. Hence the pattern of binding to these reveals the sequence-specificity of the middle finger.

The detailed procedure is as described previously (Choo and Kug, 1994). Briefly, 5'-biotinylated positionally randomised oligonucleotide libraries, containing Zif268 operator variants, are synthesised by primer extension as described. DNA libraries (2 pmol/well) are added to streptavidin-coated ELISA wells (Boehringer-Mannheim) in PBS containing 50 µM $ZnCl_2$ (PBS/Zn). Phage solution (overnight bacteria/phage culture supernatant solutions diluted 1:1 in PBS/Zn containing 4% Marvel, 2% Tween®-20 detergent and 20 µg/ml sonicated salmon sperm DNA) are applied to each well (50 µl/well). Binding is allowed to proceed for one hour at 20° C. Unbound phage are removed by washing 6 times with PBS/Zn containing 1% Tween®-20 detergent, then washing 3 times with PBS/Zn. Bound phage are detected by ELISA with horseradish peroxidase-conjugated anti-M13 IgG (Pharmacia Biotech) and quantitated using SOFTMAX 2.32 (Molecular Devices).

Figure 6:
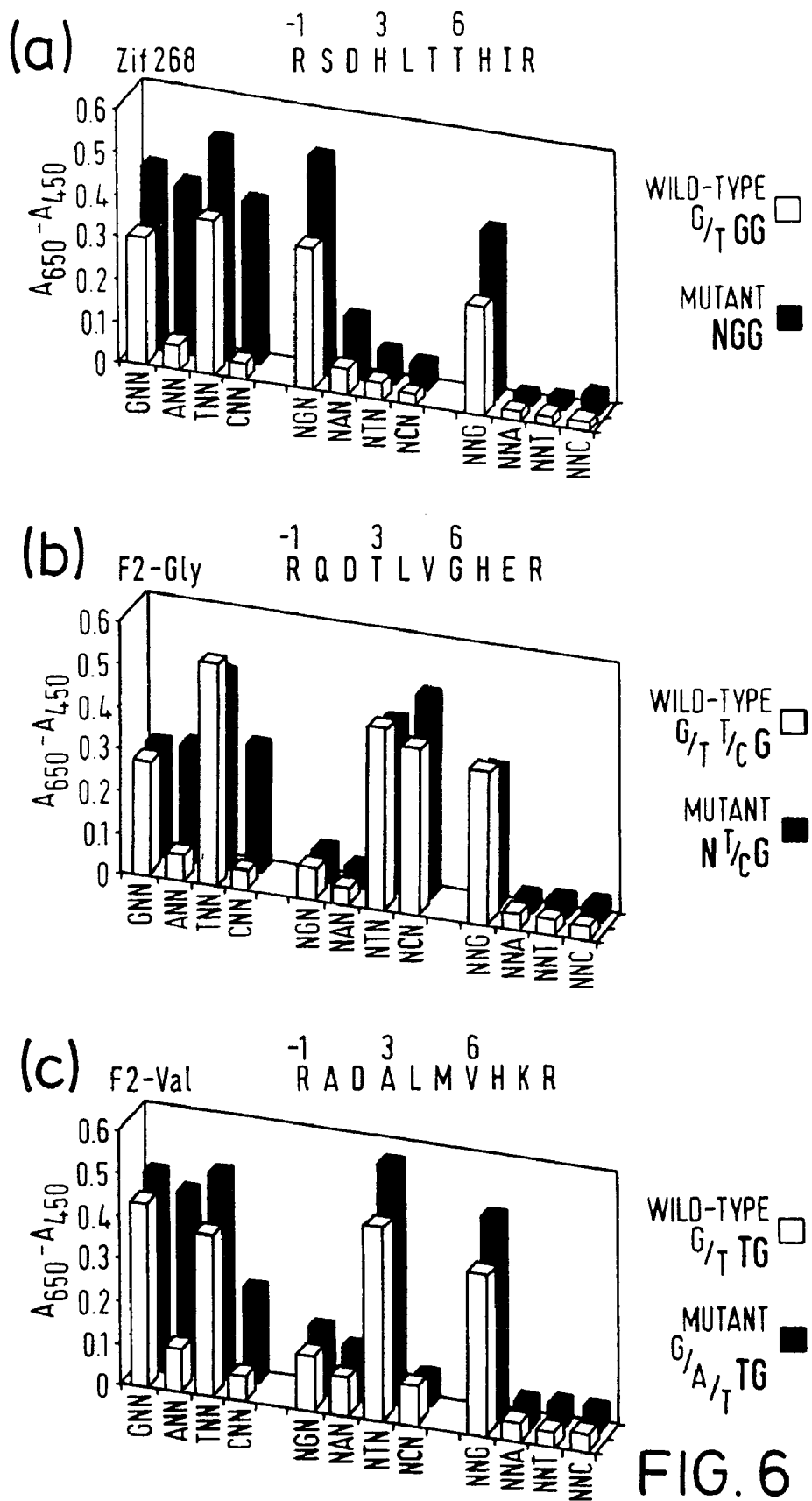
Figure 6:
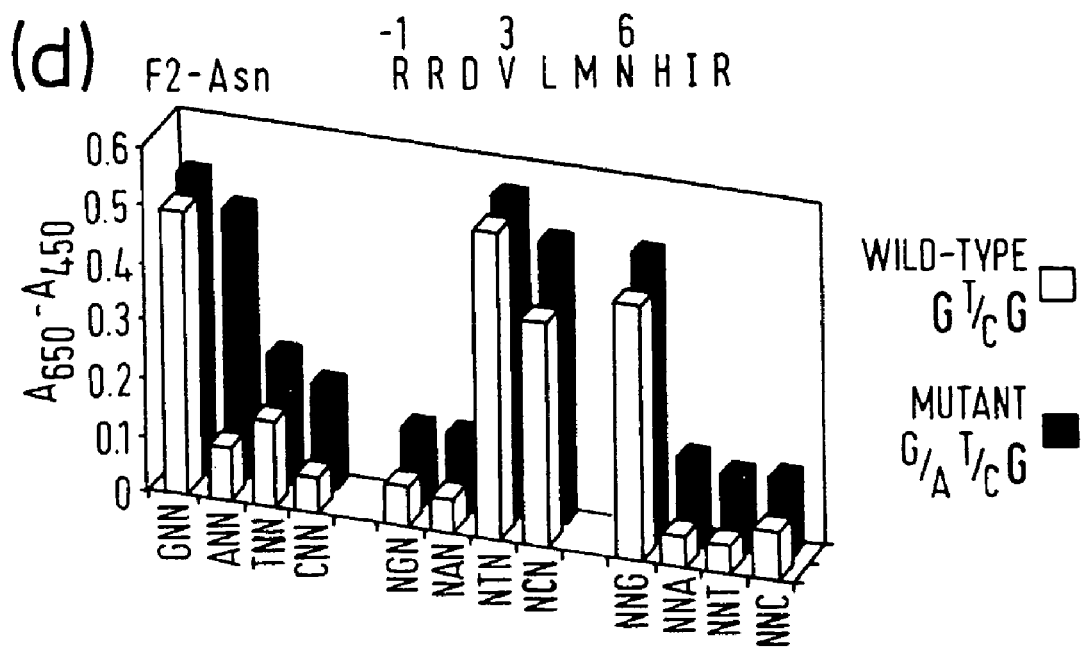
Figure 6:
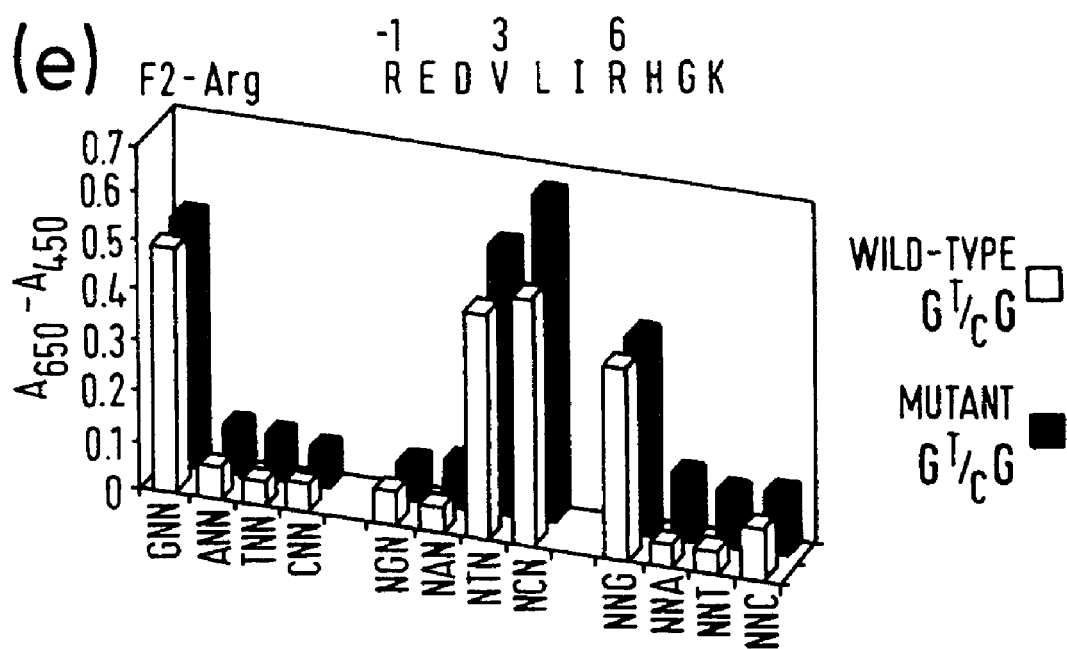
Figure 7A:
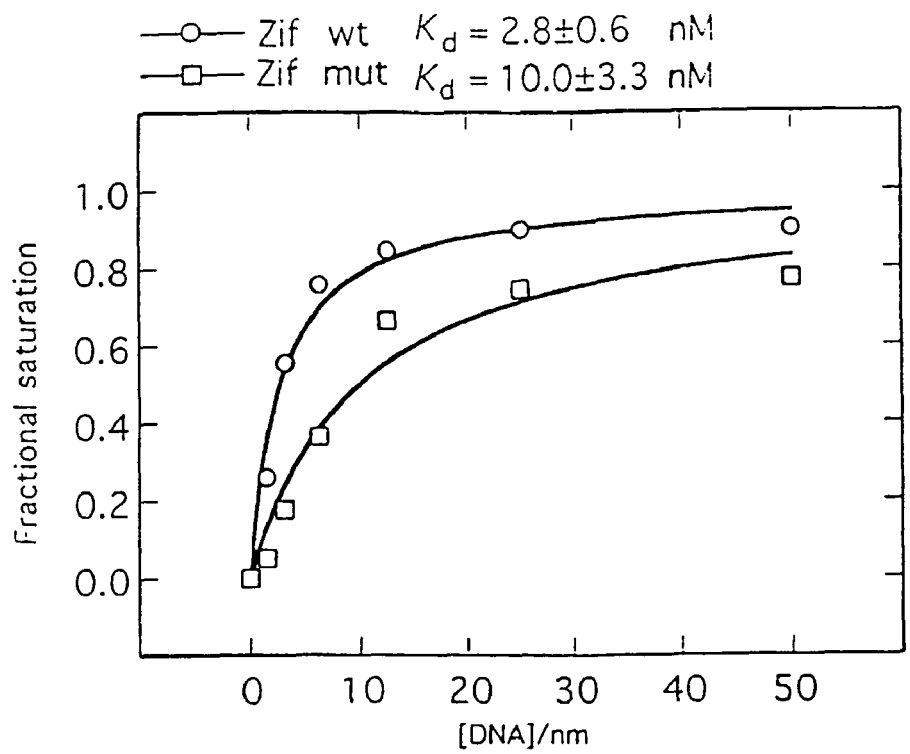

FIG. 6 shows that deleting Asp2 from finger 3 generally alters the pattern of acceptable bases, in the 'middle' triplet, which is conventionally regarded as the binding site for finger 2. As would be expected, according to the hypothesis set out in the introduction, the mutation affects binding at the 5' position, while the specificity at the middle and 3' position remains unchanged.

The mutation generally leads to a broadening of specificity, for instance in Zif268 where removal of Asp2 in finger 3 results in a protein which is unable to discriminate the 5' base of the middle triplet (FIG. 6a). However, the expectation that a new 5' base-specificity for the mutants might correlate to the identity of position 6 in finger 2, is not borne out. For example F2-Gly would be expected to lose sequence discrimination but, although specificity is adversely affected, a slight preference for T is discernible (FIG. 6b). Similarly, F2-Val and F2-Asn which might have been expected to acquire specificity for one nucleotide, instead have their specificities altered by the mutation (FIG. 6c, d)—the F2-Val mutant allows G, A and T but not C, and the F2-Asn mutant appears to discriminate against both pyrimidines. In the absence of a larger database it is not possible to deduce whether these apparent specificities are the result of amino acid-base contacts from position 6 of finger 2, and if so whether these are general interactions which should be regarded as recognition rules. The apparent discrimination of F2-Gly in particular, suggests that this is unlikely to be the case, but rather that in these particular examples, other mechanisms are involved in determining sequence bias.

In contrast to the loss of discrimination seen for the other four peptides. F2-Arg continues to specify guanine in the 5' position of the middle triplet regardless of the mutation in finger 3 (FIG. 3e). In this case, the specificity is derived from the strong interaction between guanine and Arg6 in finger 2. This contact has been observed a number of times in zinc finger co-crystal structures (Pavletich, N. P. & Pabo, C. O. (1993) Science 261, 1701-1707; Fairall, L., Schwabe, J. W. R., Chapman, L., Finch, J. T. & Rhodes, D. (1993) Nature (London) 366, 483-487; Fairall, L., Schwabe, J. W. R., Chapman, L., Finch, J. T. & Rhodes. D. (1993) Nature (London) 366, 483-487; Kim, C. & Berg, J. M. (1996) Nature Str. Biol. 3, 940-945) and is the only recognition rule which relates amino acid identity at position 6 to a nucleotide preference at the 5' position of a cognate triplet (Choo, Y. & Klug, A. (1997) Curr. Opin. Str. Biol. 7, 117-125). This interaction is compatible with, but not dependent on, a contact to the same base-pair from Asp2 of the following finger (FIG. 7c). Recognition of this base-pair can thus be synergistic, with the specificity potentially deriving from contacts contributed by two adjacent fingers.

This finding explains the restricted sequence specificity of fingers selected from phage display libraries based on Zif268 (Choo and Klug, 1994) and may also account for the failure to select zinc finger phage which bind to triplets with a 5' cytosine or adenine (Rebar. E. J. & Pabo, C. O. (1994) Science 263, 671-673; Jamieson. A. C., Kim. S.-H. & Wells, J. A. (1994) Biochemistry 33, 5689-5695). FIG. 6 shows that Asp2 of Zif268 finger 3 specifically excludes adenine and cytosine from the 5' position of the middle triplet. When this interaction is deleted, one or both of these bases become acceptable.

Preliminary modelling studies suggest that a number of amino acid residues other than aspartate may be able to make contacts to the parallel DNA strand. For instance histidine in position 2 might make a cross-strand contact to G or T while maintaining the buttress to Arg-1. Interestingly, phage selections from randomised C-terminal finger libraries have yielded several fingers with His2, and Leu or Ser at position 1 which may also influence the binding specificity (Greisman, H. A. & Pabo, C. O. (1997) Science 275, 657-661). The crystal structures of zinc finger-DNA complexes show that Ser2 is also capable of an analogous contact to the parallel DNA strand Pavletich, et al., 1993; Kim et al., 1996). Since serine is present in about 60% of all zinc fingers (Jacobs, G. (1993) Ph.D. thesis, Cambridge Univ., Cambridge, U.K.) and can act as a donor or acceptor of a hydrogen bond, it would be surprising if this amino acid at position 2 are generally capable of contributing to the binding specificity. Rather, this contact probably stabilises the protein-DNA complex, and will be a useful device in the design of zinc finger proteins with high affinity for DNA (Choo et al., 1997). It should also be noted that Ser at position 2 has been observed in the Tramtrack structure to contact the 3' base of a triplet in the antiparallel DNA strand, although this requires a deformation of the DNA (Fairall et al., 1993).

Figure 7B:
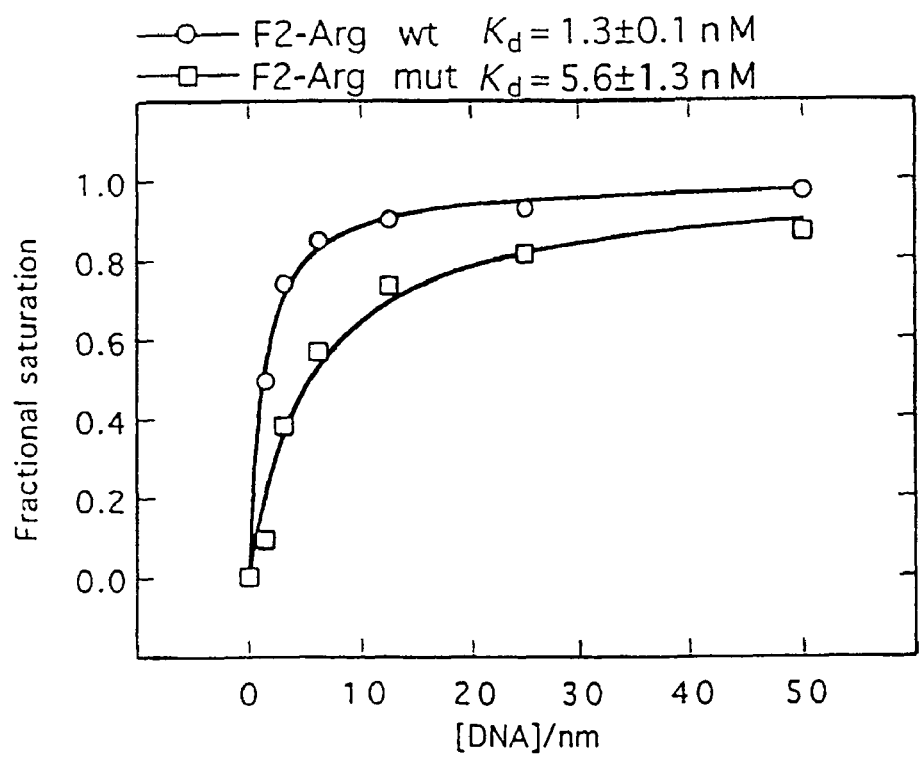

To determine the contribution of Asp2 in finger 3 to the binding strength, apparent equilibrium dissociation constants are determined for Zif268 and F2-Arg before and after the Ala mutation (FIG. 7). Procedures are as described previously (Choo and Klug, 1994). Briefly, appropriate concentrations of 5'-biotinylated DNA binding sites are added to equal volumes of phage solution described above. Binding is allowed to proceed for one hour at 20° C. DNA is captured with streptavidin-coated paramagnetic beads (500 µg/well). The beads are washed 6 times with PBS/Zn containing 1% Tween®-20 detergent, then 3 times with PBS/Zn. Bound phage are detected by ELISA with horseradish peroxidase-conjugated anti-M13 IgG (Pharmacia Biotech) and quantitated using SOFTMAX 2.32 (Molecular Devices). Binding data are plotted and analysed using Kaleidagraph (Abelbeck Software).

Both mutants show approximately a four-fold reduction in affinity for their respective binding sites under the conditions used. The reduction is likely a direct result of abolishing contacts from Asp2, rather than a consequence of changes in binding specificity at the 5' position of the middle triplet, since the mutant Zif268 loses all specificity while F2-Arg registers no change in specificity. However, note that two stabilising interactions are abolished: an intramolecular buttressing interaction with Arg-1 on finger 3 and also the intermolecular contact with the secondary DNA strand. An independent comparison of wild-type Zif268 binding to its consensus binding site flanked by G/T or A/C also found a five-fold reduction in affinity for those sites which are unable to satisfy a contact from Asp2 to the secondary DNA strand (Smirnoff, A. H. & Milbrandt, J. (1995) Mol. Cel. Biol. 15, 2275-2287). While the effects of perturbations in the DNA structure cannot be discounted in this case, the results of both experiments would seem to suggest that the reduction in binding affinity results from loss of the protein-DNA contact. Nevertheless, the intramolecular contact between positions −1 and 2 in a zinc finger, is a further level of synergy which may have to be taken into account before the full picture emerges, describing the possible networks of contacts which occur at the protein-DNA interface in the region of the overlapping subsites.

The invention claimed is:

1. A method for designing a nucleic acid binding protein that binds to a target nucleotide sequence, wherein the binding protein comprises a plurality of zinc fingers, and adjacent zinc fingers bind synergistically to overlapping quadruplet target subsites, and wherein the method comprises:

i) selecting a quadruplet within the target nucleotide sequence;

ii) designing the binding protein such that binding of a zinc finger to the quadruplet is obtained by choosing the sequence of particular residues of the zinc finger depending on the nucleotide sequence of the quadruplet, as follows:

a) if base 4 in the quadruplet is A, then position +6 in the α-helix is Gln and position ++2 is not Asp;

b) if base 4 in the quadruplet is C, then position +6 in the α-helix may be any residue, as long as position ++2 in the α-helix is not Asp.

2. The method according to claim 1, wherein binding to base 4 of the quadruplet by a zinc finger is additionally determined as follows:

c) if base 4 in the quadruplet is G, then position +6 in the α-helix is Arg, or position +6 is Ser or Thr and position ++2 is Asp;

d) if base 4 in the quadruplet is T, then position +6 in the α-helix is Ser or Thr and position ++2 is Asp.

3. A method for designing a nucleic acid binding protein that binds to a target nucleotide sequence, wherein the binding protein comprises a plurality of zinc fingers, and adjacent zinc fingers bind synergistically to overlapping quadruplet target subsites, and wherein the method comprises:

i) selecting a quadruplet within the target nucleotide sequence;

ii) designing the binding protein such that binding of a zinc finger to the quadruplet is obtained by choosing the sequence of particular residues of the zinc finger depending on the nucleotide sequence of the quadruplet, as follows:

a) if base 4 in the quadruplet is G, then position +6 in the α-helix is Arg; or position +6 is Ser or Thr and position ++2 is Asp;

b) if base 4 in the quadruplet is A, then position +6 in the α-helix is Gln and position ++2 is not Asp;

c) if base 4 in the quadruplet is T, then position +6 in the α-helix is Ser or Thr and position ++2 is Asp;
d) if base 4 in the quadruplet is C, then position +6 in the α-helix may be any amino acid, provided that position ++2 in the α-helix is not Asp;
e) if base 3 in the quadruplet is G, then position +3 in the α-helix is His;
f) if base 3 in the quadruplet is A, then position +3 in the α-helix is Asn;
g) if base 3 in the quadruplet is T, then position +3 in the α-helix is Ala, Ser or Val; provided that if it is Ala, then the residues at −1 or +6 are small residues;
h) if base 3 in the quadruplet is C, then position +3 in the α-helix is Ser, Asp, Glu, Leu, Thr or Val;
i) if base 2 in the quadruplet is G, then position −1 in the α-helix is Arg;
j) if base 2 in the quadruplet is A, then position −1 in the α-helix is Gln;
k) if base 2 in the quadruplet is T, then position −1 in the α-helix is Asn or Gln;
l) if base 2 in the quadruplet is C, then position −1 in the α-helix is Asp;
m) if base 1 in the quadruplet is G, then position +2 is Asp;
n) if base 1 in the quadruplet is A, then position +2 is not Asp;
o) if base 1 in the quadruplet is C, then position +2 is not Asp;
p) if base 1 in the quadruplet is T, then position +2 is Ser or Thr.

4. The method of claims 3, wherein each zinc finger has the general primary structure with positions numbered such that position 1 is the first position of an alpha helix

−1 1 2 3 4 5 6 7 8 9

$X^a$ Cys $X_{2-4}$ Cys-$X_{2-3}$-Phe-$X^c$-X-X-X-X-Leu-X-X-His-X-X-$X^b$ His/Cys, SEQ ID NO:25) wherein X (including $X^a$, $X^b$ and $X^c$) is any amino acid.

5. The method according to claim 4, wherein $X^a$ is Phe/Tyr-X or Pro-Phe/Tyr-X.

6. The method according to claim 5, wherein $X_{2-4}$ is selected from any one of:
Ser-X, Glu-X, Lys-X, Thr-X, Pro-X and Arg-X.

7. The method according to claim 4, wherein $X^b$ is Thr or Ile.

8. The method according to claim 4, wherein $X_{2-3}$ is Gly-Lys-Ala, Gly-Lys-Cys, Gly-Lys-Ser, Gly-Lys-Gly, Met-Arg-Asn or Met-Arg.

9. The method according to claim 4, wherein at least one zinc finger is linked to a linker that is Thr-Gly-Glu-Lys (SEQ ID NO: 4) or Thr-Gly-Glu-Lys-Pro (SEQ ID NO: 5).

10. The method according to claim 4, wherein position +9 is Arg or Lys.

11. The method according to claim 4, wherein positions +1, +5 and +8 are not occupied by any one of the hydrophobic amino acids Phe, Trp or Tyr.

12. The method according to claim 11, wherein positions +1, +5 and +8 are occupied by the residues Lys, Thr and Gln respectively.

13. A method for designing a nucleic acid binding protein which binds a target nucleic acid sequence, comprising the steps of:
a) selecting a model zinc finger domain from the group consisting of naturally occurring zinc fingers and consensus zinc fingers; and
b) mutating the finger according to the rules of claim 2.

14. A method for designing a nucleic acid binding protein which binds a target nucleic acid sequence, comprising the steps of:
a) selecting a model zinc finger domain from the group consisting of naturally occurring zinc fingers and consensus zinc fingers; and
b) mutating the finger according to the rules of claim 4.

15. The method according to claim 14, wherein the model zinc finger is a consensus zinc finger whose structure is selected from the group consisting of the consensus structure Pro-Tyr-Lys-Cys-Pro-Glu-Cys-Gly-Lys-Ser-Phe-Ser-Gln-Lys-Ser-Asp-Leu-Val-Lys-His-Gln-Arg-Thr-His-Thr-Gly (SEQ ID NO: 6), and the consensus structure Pro-Tyr-Lys-Cys-Ser-Glu-Cys-Gly-Lys-Ala-Phe-Ser-Gln-Lys-Ser-Asn; Leu-Thr-Arg-His-Gln-Arg-Ile-His-Thr-Gly-Glu-Lys-Pro (SEQ ID NO: 7).

16. The method according to claim 14, wherein the model zinc finger is a naturally-occurring zinc finger of Zif268.

17. The method according to claim 16, wherein the model zinc finger is finger 2 of Zif 268.

18. The method according to claim 14, wherein the binding protein comprises two or more zinc finger binding motifs, placed N-terminus to C-terminus.

19. The method according to claim 15, wherein the N-terminal zinc finger is preceded by a leader peptide having the sequence Met-Ala-Glu-Glu-Lys-Pro (SEQ ID NO: 8).

20. The method of any one of claims 1, 2 and 3, wherein a plurality of overlapping quadruplets are selected within the target sequence.

21. The method of claim 20, wherein step (ii) comprises designing a first zinc finger that binds to a first of the overlapping quadruplets and a second zinc finger that binds to a second of the overlapping quadruplets.

* * * * *

SEQUENCE LISTING

```
<160> NUMBER OF SEQ ID NOS: 25

<210> SEQ ID NO 1
<211> LENGTH: 264
<212> TYPE: DNA
<213> ORGANISM: Artificial
<220> FEATURE:
<223> OTHER INFORMATION: Synthetic nucleic acid encoding binding protein
<220> FEATURE:
<221> NAME/KEY: CDS
<222> LOCATION: (1)..(264)

<400> SEQUENCE: 1 gca gaa gag aag cct ttt cag tgt cga atc tgc atg cgt aac ttc agc      48
Ala Glu Glu Lys Pro Phe Gln Cys Arg Ile Cys Met Arg Asn Phe Ser
1               5                   10                  15 gat cgt agt agt ctt acc cgc cac acg agg acc cac aca ggc gag aag      96
Asp Arg Ser Ser Leu Thr Arg His Thr Arg Thr His Thr Gly Glu Lys
                20                  25                  30 cct ttt cag tgt cga atc tgc atg cgt aac ttc agc agg agc gat aac     144
Pro Phe Gln Cys Arg Ile Cys Met Arg Asn Phe Ser Arg Ser Asp Asn
            35                  40                  45 ctt acg aga cac cta agg acc cac aca ggc gag aag cct ttt cag tgt     192
Leu Thr Arg His Leu Arg Thr His Thr Gly Glu Lys Pro Phe Gln Cys
        50                  55                  60 cga atc tgc atg cgt aac ttc agg caa gct gat cat ctt caa gag cac     240
Arg Ile Cys Met Arg Asn Phe Arg Gln Ala Asp His Leu Gln Glu His
65                  70                  75                  80 cta aag acc cac aca ggc gag aag                                     264
Leu Lys Thr His Thr Gly Glu Lys
                85

<210> SEQ ID NO 2
<211> LENGTH: 88
<212> TYPE: PRT
<213> ORGANISM: Artificial
<220> FEATURE:
<223> OTHER INFORMATION: Synthetic binding protein

<400> SEQUENCE: 2

Ala Glu Glu Lys Pro Phe Gln Cys Arg Ile Cys Met Arg Asn Phe Ser
1               5                   10                  15

Asp Arg Ser Ser Leu Thr Arg His Thr Arg Thr His Thr Gly Glu Lys
                20                  25                  30

Pro Phe Gln Cys Arg Ile Cys Met Arg Asn Phe Ser Arg Ser Asp Asn
            35                  40                  45

Leu Thr Arg His Leu Arg Thr His Thr Gly Glu Lys Pro Phe Gln Cys
        50                  55                  60

Arg Ile Cys Met Arg Asn Phe Arg Gln Ala Asp His Leu Gln Glu His
65                  70                  75                  80

Leu Lys Thr His Thr Gly Glu Lys
                85
```

```
<210> SEQ ID NO 3
<211> LENGTH: 24
<212> TYPE: PRT
<213> ORGANISM: Artificial
<220> FEATURE:
<223> OTHER INFORMATION: Synthetic formula motif
<220> FEATURE:
<221> NAME/KEY: MOD_RES
<222> LOCATION: (1)..(1)
<223> OTHER INFORMATION: Xaa = Any amino acid
<220> FEATURE:
<221> NAME/KEY: MOD_RES
<222> LOCATION: (3)..(4)
<223> OTHER INFORMATION: Xaa = Any amino acid
<220> FEATURE:
<221> NAME/KEY: MOD_RES
<222> LOCATION: (5)..(6)
<223> OTHER INFORMATION: Xaa = Any amino acid or absent
<220> FEATURE:
<221> NAME/KEY: MOD_RES
<222> LOCATION: (8)..(9)
<223> OTHER INFORMATION: Xaa = Any amino acid
<220> FEATURE:
<221> NAME/KEY: MOD_RES
<222> LOCATION: (10)..(10)
<223> OTHER INFORMATION: Xaa = Any amino acid or absent
<220> FEATURE:
<221> NAME/KEY: MOD_RES
<222> LOCATION: (12)..(16)
<223> OTHER INFORMATION: Xaa = Any amino acid
<220> FEATURE:
<221> NAME/KEY: MOD_RES
<222> LOCATION: (18)..(19)
<223> OTHER INFORMATION: Xaa = Any amino acid
<220> FEATURE:
<221> NAME/KEY: MOD_RES
<222> LOCATION: (21)..(23)
<223> OTHER INFORMATION: Xaa = Any amino acid
<220> FEATURE:
<221> NAME/KEY: MOD_RES
<222> LOCATION: (24)..(24)
<223> OTHER INFORMATION: Xaa = His modified by a linker sequence

<400> SEQUENCE: 3

Xaa Cys Xaa Xaa Xaa Xaa Cys Xaa Xaa Xaa Phe Xaa Xaa Xaa Xaa Xaa
1               5                   10                  15

Leu Xaa Xaa His Xaa Xaa Xaa Xaa
            20

<210> SEQ ID NO 4
<211> LENGTH: 4
<212> TYPE: PRT
<213> ORGANISM: Artificial
<220> FEATURE:
<223> OTHER INFORMATION: Synthetic linker

<400> SEQUENCE: 4

Thr Gly Glu Lys
1

<210> SEQ ID NO 5
<211> LENGTH: 5
<212> TYPE: PRT
<213> ORGANISM: Artificial
<220> FEATURE:
<223> OTHER INFORMATION: Synthetic linker

<400> SEQUENCE: 5

Thr Gly Glu Lys Pro
1               5

<210> SEQ ID NO 6
```

```
<211> LENGTH: 26
<212> TYPE: PRT
<213> ORGANISM: Artificial
<220> FEATURE:
<223> OTHER INFORMATION: Synthetic consensus structure

<400> SEQUENCE: 6

Pro Tyr Lys Cys Pro Glu Cys Gly Lys Ser Phe Ser Gln Lys Ser Asp
1               5                   10                  15

Leu Val Lys His Gln Arg Thr His Thr Gly
            20                  25

<210> SEQ ID NO 7
<211> LENGTH: 29
<212> TYPE: PRT
<213> ORGANISM: Artificial
<220> FEATURE:
<223> OTHER INFORMATION: Synthetic consensus structure

<400> SEQUENCE: 7

Pro Tyr Lys Cys Ser Glu Cys Gly Lys Ala Phe Ser Gln Lys Ser Asn
1               5                   10                  15

Leu Thr Arg His Gln Arg Ile His Thr Gly Glu Lys Pro
            20                  25

<210> SEQ ID NO 8
<211> LENGTH: 6
<212> TYPE: PRT
<213> ORGANISM: Artificial
<220> FEATURE:
<223> OTHER INFORMATION: Synthetic leader peptide

<400> SEQUENCE: 8

Met Ala Glu Glu Lys Pro
1               5

<210> SEQ ID NO 9
<211> LENGTH: 28
<212> TYPE: PRT
<213> ORGANISM: Artificial
<220> FEATURE:
<223> OTHER INFORMATION: Synthetic zinc finger motif

<400> SEQUENCE: 9

Phe Gln Cys Arg Ile Cys Met Arg Asn Phe Ser Asp Arg Ser Ser Leu
1               5                   10                  15

Thr Arg His Thr Arg Thr His Thr Gly Glu Lys Pro
            20                  25

<210> SEQ ID NO 10
<211> LENGTH: 28
<212> TYPE: PRT
<213> ORGANISM: Artificial
<220> FEATURE:
<223> OTHER INFORMATION: Synthetic zinc finger motif

<400> SEQUENCE: 10

Phe Gln Cys Arg Ile Cys Met Arg Asn Phe Ser Asp Arg Ser His Leu
1               5                   10                  15

Thr Arg His Thr Arg Thr His Thr Gly Glu Lys Pro
            20                  25

<210> SEQ ID NO 11
<211> LENGTH: 27
<212> TYPE: PRT
```

<213> ORGANISM: Artificial
<220> FEATURE:
<223> OTHER INFORMATION: Synthetic zinc finger motif

<400> SEQUENCE: 11

Phe Gln Cys Arg Ile Cys Met Arg Asn Phe Ser Asp Arg Ser Asn Leu
1               5                   10                  15

Thr Arg His Thr Arg Thr His Thr Gly Glu Lys
            20                  25

<210> SEQ ID NO 12
<211> LENGTH: 27
<212> TYPE: DNA
<213> ORGANISM: Artificial
<220> FEATURE:
<223> OTHER INFORMATION: Synthetic DNA

<400> SEQUENCE: 12
gtggtgggcg ccggcggtgt gggcaag                                           27

<210> SEQ ID NO 13
<211> LENGTH: 27
<212> TYPE: DNA
<213> ORGANISM: Artificial
<220> FEATURE:
<223> OTHER INFORMATION: Synthetic DNA

<400> SEQUENCE: 13
gtggtgggcg ccgtcggtgt gggcaag                                           27

<210> SEQ ID NO 14
<211> LENGTH: 34
<212> TYPE: PRT
<213> ORGANISM: Artificial
<220> FEATURE:
<223> OTHER INFORMATION: Synthetic zinc finger motif

<400> SEQUENCE: 14

Met Ala Glu Glu Lys Pro Phe Gln Cys Arg Ile Cys Met Arg Asn Phe
1               5                   10                  15

Ser Asp Arg Ser Ser Leu Thr Arg His Thr Arg Thr His Thr Gly Glu
            20                  25                  30

Lys Pro

<210> SEQ ID NO 15
<211> LENGTH: 27
<212> TYPE: PRT
<213> ORGANISM: Artificial
<220> FEATURE:
<223> OTHER INFORMATION: Synthetic zinc finger motif

<400> SEQUENCE: 15

Phe Gln Cys Arg Ile Cys Met Arg Asn Phe Ser Asp Arg Ser Ser Leu
1               5                   10                  15

Thr Arg His Thr Arg Thr His Thr Gly Glu Lys
            20                  25

<210> SEQ ID NO 16
<211> LENGTH: 36
<212> TYPE: PRT
<213> ORGANISM: Artificial
<220> FEATURE:
<223> OTHER INFORMATION: Synthetic zinc finger motif

<400> SEQUENCE: 16

Trp Ala Glu Glu Arg Pro Tyr Ala Cys Pro Val Glu Ser Cys Asp Arg
1               5                   10                  15

Arg Phe Ser Arg Ser Asp Glu Leu Thr Arg His Ile Arg Ile His Thr
            20                  25                  30

Gly Gln Lys Pro
        35

<210> SEQ ID NO 17
<211> LENGTH: 28
<212> TYPE: PRT
<213> ORGANISM: Artificial
<220> FEATURE:
<223> OTHER INFORMATION: Synthetic zinc finger motif
<220> FEATURE:
<221> NAME/KEY: MOD_RES
<222> LOCATION: (12)..(15)
<223> OTHER INFORMATION: Xaa = Any amino acid
<220> FEATURE:
<221> NAME/KEY: MOD_RES
<222> LOCATION: (17)..(18)
<223> OTHER INFORMATION: Xaa = Any amino acid
<220> FEATURE:
<221> NAME/KEY: MOD_RES
<222> LOCATION: (20)..(21)
<223> OTHER INFORMATION: Xaa = Any amino acid

<400> SEQUENCE: 17

Phe Gln Cys Arg Ile Cys Trp Arg Asn Phe Ser Xaa Xaa Xaa Xaa Leu
1               5                   10                  15

Xaa Xaa His Xaa Xaa Thr His Thr Gly Glu Lys Pro
            20                  25

<210> SEQ ID NO 18
<211> LENGTH: 28
<212> TYPE: PRT
<213> ORGANISM: Artificial
<220> FEATURE:
<223> OTHER INFORMATION: Synthetic zinc finger motif

<400> SEQUENCE: 18

Phe Ala Cys Asp Ile Cys Gly Arg Lys Phe Ala Arg Ser Asp Glu Arg
1               5                   10                  15

Lys Arg His Thr Lys Ile His Leu Arg Gln Lys Asp
            20                  25

<210> SEQ ID NO 19
<211> LENGTH: 12
<212> TYPE: PRT
<213> ORGANISM: Artificial
<220> FEATURE:
<223> OTHER INFORMATION: Synthetic zinc finger motif

<400> SEQUENCE: 19

Arg Ser Asp His Leu Thr Thr His Ile Arg Thr His
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic zinc finger motif

<400> SEQUENCE: 20

Arg Gln Asp Thr Leu Val Gly His Glu Arg Thr His
1               5                   10

```
<210> SEQ ID NO 21
<211> LENGTH: 12
<212> TYPE: PRT
<213> ORGANISM: Artificial
<220> FEATURE:
<223> OTHER INFORMATION: Synthetic zinc finger motif

<400> SEQUENCE: 21

Arg Ala Asp Ala Leu Met Val His Lys Arg Thr His
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic zinc finger motif

<400> SEQUENCE: 22

Arg Arg Asp Val Leu Met Asn His Ile Arg Thr His
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic zinc finger motif

<400> SEQUENCE: 23

Arg Glu Asp Val Leu Ile Arg His Gly Lys Thr His
1               5                   10

<210> SEQ ID NO 24
<211> LENGTH: 31
<212> TYPE: PRT
<213> ORGANISM: Artificial
<220> FEATURE:
<223> OTHER INFORMATION: Syntehtic formula motif
<220> FEATURE:
<221> NAME/KEY: MOD_RES
<222> LOCATION: (1)..(2)
<223> OTHER INFORMATION: Xaa = Any amino acid or absent
<220> FEATURE:
<221> NAME/KEY: MOD_RES
<222> LOCATION: (4)..(8)
<223> OTHER INFORMATION: Xaa = Any amino acid or absent
<220> FEATURE:
<221> NAME/KEY: MOD_RES
<222> LOCATION: (10)..(23)
<223> OTHER INFORMATION: Xaa = Any amino acid or absent
<220> FEATURE:
<221> NAME/KEY: MOD_RES
<222> LOCATION: (25)..(30)
<223> OTHER INFORMATION: Xaa = Any amino acid
<220> FEATURE:
<221> NAME/KEY: MOD_RES
<222> LOCATION: (31)..(31)
<223> OTHER INFORMATION: Xaa = His or Cys

<400> SEQUENCE: 24

Xaa Xaa Cys Xaa Xaa Xaa Xaa Xaa Cys Xaa Xaa Xaa Xaa Xaa Xaa
1               5                   10                  15

Xaa Xaa Xaa Xaa Xaa Xaa Xaa His Xaa Xaa Xaa Xaa Xaa Xaa Xaa
                20                  25                  30

<210> SEQ ID NO 25
<211> LENGTH: 24
```

-continued

```
<212> TYPE: PRT
<213> ORGANISM: Artificial
<220> FEATURE:
<223> OTHER INFORMATION: Synthetic formula motif
<220> FEATURE:
<221> NAME/KEY: MOD_RES
<222> LOCATION: (1)..(1)
<223> OTHER INFORMATION: Xaa = Any amino acid
<220> FEATURE:
<221> NAME/KEY: MOD_RES
<222> LOCATION: (3)..(4)
<223> OTHER INFORMATION: Xaa = Any amino acid
<220> FEATURE:
<221> NAME/KEY: MOD_RES
<222> LOCATION: (5)..(6)
<223> OTHER INFORMATION: Xaa = Any amino acid or absent
<220> FEATURE:
<221> NAME/KEY: MOD_RES
<222> LOCATION: (8)..(9)
<223> OTHER INFORMATION: Xaa = Any amino acid
<220> FEATURE:
<221> NAME/KEY: MOD_RES
<222> LOCATION: (10)..(10)
<223> OTHER INFORMATION: Xaa = Any amino acid or absent
<220> FEATURE:
<221> NAME/KEY: MOD_RES
<222> LOCATION: (12)..(16)
<223> OTHER INFORMATION: Xaa = Any amino acid
<220> FEATURE:
<221> NAME/KEY: MOD_RES
<222> LOCATION: (18)..(19)
<223> OTHER INFORMATION: Xaa = Any amino acid
<220> FEATURE:
<221> NAME/KEY: MOD_RES
<222> LOCATION: (21)..(23)
<223> OTHER INFORMATION: Xaa = Any amino acid
<220> FEATURE:
<221> NAME/KEY: MOD_RES
<222> LOCATION: (24)..(24)
<223> OTHER INFORMATION: Xaa = Cys or His

<400> SEQUENCE: 25

Xaa Cys Xaa Xaa Xaa Xaa Cys Xaa Xaa Xaa Phe Xaa Xaa Xaa Xaa Xaa
1               5                   10                  15

Leu Xaa Xaa His Xaa Xaa Xaa Xaa
            20
```